(12) United States Patent
Dong et al.

(10) Patent No.: US 9,725,398 B2
(45) Date of Patent: Aug. 8, 2017

(54) BENZENE-BASED DIPHOSPHINE LIGANDS FOR ALKOXYCARBONYLATION

(71) Applicant: EVONIK DEGUSSA GMBH, Essen (DE)

(72) Inventors: Kaiwu Dong, Bo Zhou (CN); Helfried Neumann, Rostock (DE); Ralf Jackstell, Cuxhaven Altenwalde (DE); Matthias Beller, Ostseebad Nienhagen (DE); Robert Franke, Marl (DE); Dieter Hess, Marl (DE); Katrin Marie Dyballa, Reckinghausen (DE); Dirk Fridag, Haltern am See (DE); Frank Geilen, Haltern am See (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 15/213,441

(22) Filed: Jul. 19, 2016

(65) Prior Publication Data
US 2017/0022137 A1    Jan. 26, 2017

(30) Foreign Application Priority Data
Jul. 23, 2015   (DE) .................. 10 2015 213 918

(51) Int. Cl.
*C07F 9/28* (2006.01)
*B01J 31/18* (2006.01)
(Continued)

(52) U.S. Cl.
CPC ........... *C07C 67/38* (2013.01); *B01J 31/2295* (2013.01); *B01J 31/24* (2013.01); *B01J 31/2404* (2013.01);
(Continued)

(58) Field of Classification Search
CPC .................................. C07F 9/28; B01J 31/18
(Continued)

(56) References Cited

U.S. PATENT DOCUMENTS

| 6,335,471 B1 | 1/2002 | Eastham et al. |
| 6,433,242 B1 | 8/2002 | Wiese |
| 8,969,560 B2 * | 3/2015 | Eastham ............. B01J 31/0215 502/162 |

FOREIGN PATENT DOCUMENTS

| DE | 1 029 839 A1 | 8/2009 |
| DE | 10 2008 007081 A1 | 8/2009 |

(Continued)

OTHER PUBLICATIONS

Khokarale, S. G. et al. Zwitterion enhanced performance in palladium-phosphine catalyzed ethylene methoxycarbonylation. Catalysis Communications 44, 2014, pp. 73-75.

Clegg, William, et al, Highly active and selective catalysts for the production of methyl propanoate via the methoxycarbonylation of ethane. Chem. Commun. 1999, pp. 1877-1878.

Armarego, Wilfred L.F., et al. Purification of Laboratory Chemicals, Butterworth Heinemann (Elsevier), 6th edition, Oxford 2009. (index provided).

Harris, Robin K. et al. NMR Nomenclature, Nuclear Spin Properties and Conventions for Chemical Shifts. Pure Appl. Chem., 2001, 73, pp. 1795-1818.

Harris, Robin K. et al. Further Conventions for NMR Shielding and Chemical Shifts, Pure Appl. Chem., 2008, 80, pp. 59-84.

Köppe, Ralf, et al. Quntenchemische and Experimentelle Untersuchungen zur Stabilität and Struktur von GaAs$_5$und InAs$_5$. Angew. Chem. 2004, 43, 2222-2226.

(Continued)

*Primary Examiner* — Charanjit Aulakh
(74) *Attorney, Agent, or Firm* — Smith, Gambrell & Russell, LLP

(57) ABSTRACT

The invention relates to compounds of formula (I)

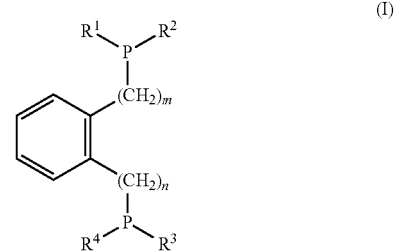

Figure 1:
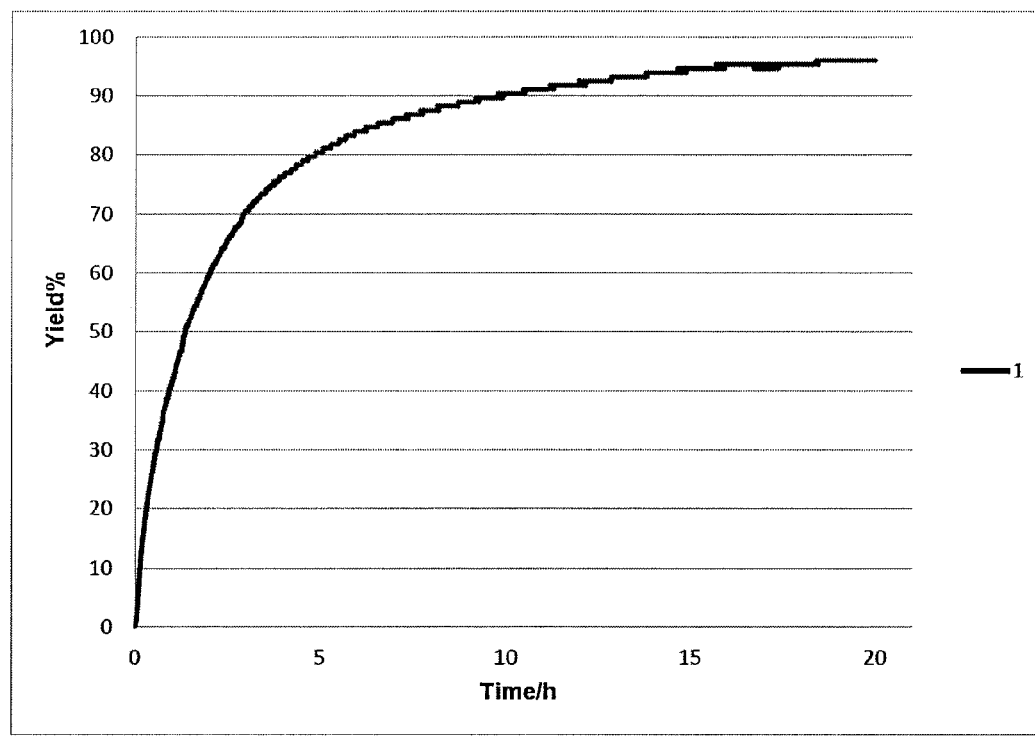

where
m and n are each independently 0 or 1;
$R^1$, $R^2$, $R^3$, $R^4$ are each independently selected from —($C_1$-$C_{12}$)-alkyl, —($C_3$-$C_{12}$)-cycloalkyl, —($C_3$-$C_{12}$)-heterocycloalkyl, —($C_6$-$C_{20}$)-aryl, —($C_3$-$C_{20}$)-heteroaryl;
at least one of the $R^1$, $R^2$, $R^3$, $R^4$ radicals is a —($C_3$-$C_{20}$)-heteroaryl radical;
and
$R^1$, $R^2$, $R^3$, $R^4$, if they are —($C_1$-$C_{12}$)-alkyl, —($C_3$-$C_{12}$)-cycloalkyl, —($C_3$-$C_{12}$)-heterocycloalkyl, —($C_6$-$C_{20}$)-aryl or —($C_3$-$C_{20}$)-heteroaryl,
may each independently be substituted by one or more substituents selected from —($C_1$-$C_{12}$)-alkyl, —($C_3$-$C_{12}$)-cycloalkyl, —($C_3$-$C_{12}$)-heterocycloalkyl, —O—($C_1$-$C_{12}$)-alkyl, —O—($C_1$-$C_{12}$)-alkyl-($C_6$-$C_{20}$)-aryl, —O—($C_3$-$C_{12}$)-cycloalkyl, —S—($C_1$-$C_{12}$)-alkyl, —S—($C_3$-$C_{12}$)-cycloalkyl, —COO—($C_1$-$C_{12}$)-alkyl, —COO—($C_3$-$C_{12}$)-cycloalkyl, —CONH—($C_1$-$C_{12}$)-alkyl, —CONH—($C_3$-$C_{12}$)-cycloalkyl, —CO—($C_1$-$C_{12}$)-alkyl, —CO—($C_3$-$C_{12}$)-cycloalkyl, —N—[($C_1$-$C_{12}$)-alkyl]$_2$, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl, —($C_3$-$C_{20}$)-heteroaryl, —($C_3$-$C_{20}$)-heteroaryl-($C_1$-$C_{12}$)-alkyl, —($C_3$-$C_{20}$)-heteroaryl-O—($C_1$-$C_{12}$)-alkyl, —COOH, —OH, —SO$_3$H, —NH$_2$, halogen;
and to the use thereof as ligands in alkoxycarbonylation.

14 Claims, 1 Drawing Sheet

(51) Int. Cl.
*C07F 15/00* (2006.01)
*C07C 67/38* (2006.01)
*C07F 9/58* (2006.01)
*C07F 9/6506* (2006.01)
*B01J 31/24* (2006.01)
*B01J 31/22* (2006.01)
*C07F 9/572* (2006.01)
*C07F 9/655* (2006.01)
*C07F 9/6553* (2006.01)
*C07F 17/02* (2006.01)

(52) U.S. Cl.
CPC ......... *B01J 31/2409* (2013.01); *C07F 9/5726* (2013.01); *C07F 9/587* (2013.01); *C07F 9/65066* (2013.01); *C07F 9/65515* (2013.01); *C07F 9/655345* (2013.01); *C07F 15/006* (2013.01); *C07F 17/02* (2013.01); *B01J 2231/321* (2013.01); *B01J 2231/49* (2013.01); *B01J 2531/0208* (2013.01); *B01J 2531/824* (2013.01); *B01J 2531/842* (2013.01)

(58) Field of Classification Search
USPC ....................................... 546/21, 2; 502/162
See application file for complete search history.

(56) References Cited

FOREIGN PATENT DOCUMENTS

WO  2011/083305 A1  7/2011
WO  2011/152358 A1  12/2011

OTHER PUBLICATIONS

Budzelaar, Peter H.M. et al. Synthesis and Coordination Chemistry of a New Class of Binucleating Ligands: Pyridyl-Substituted Diphosphines. Organometallics 1990, 9, 1222-1227.
U.S. Appl. No. 15/213,435, filed Jul. 19, 2016, Jennerjahn, et al.
U.S. Appl. No. 15/213,444, filed Jul. 19, 2016, Dong, et al.
U.S. Appl. No. 15/213,449, filed Jul. 19, 2016, Dong, et al.
U.S. Appl. No. 15/213,453, filed Jul. 19, 2016, Dong, et al.
U.S. Appl. No. 15/213,456, filed Jul. 19, 2016, Dong, et al.
European Search Report for EP16 180 045 dated Jan. 2, 2017 (1 page).
Brunner, H., et al. Enantioslective Catalyses 110. New Chiral Phosphanes Derived from Substituted Quinolines. Synthesis. Nov. 1997. 1309-1314.

* cited by examiner

BENZENE-BASED DIPHOSPHINE LIGANDS FOR ALKOXYCARBONYLATION

The invention relates to benzene-based diphosphine compounds, to metal complexes of these compounds and to the use thereof for alkoxycarbonylation.

The alkoxycarbonylation of ethylenically unsaturated compounds is a process of increasing significance. An alkoxycarbonylation is understood to mean the reaction of ethylenically unsaturated compounds (olefins) with carbon monoxide and alcohols in the presence of a metal-ligand complex to give the corresponding esters. Typically, the metal used is palladium. The following scheme shows the general reaction equation of an alkoxycarbonylation:

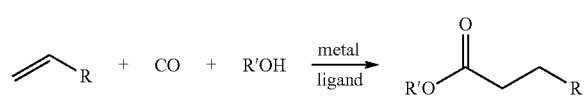

Among the alkoxycarbonylation reactions, particularly the reaction of ethene and methanol to give 3-methylpropionate (ethene methoxycarbonylation) is of significance as an intermediate step for the preparation of methyl methacrylate (S. G. Khokarale, E. J. Garcia-Suárez, J. Xiong, U. V. Mentzel, R. Fehrmann, A. Riisager, Catalysis Communications 2014, 44, 73-75). Ethene methoxycarbonylation is conducted in methanol as solvent under mild conditions with a palladium catalyst modified by phosphine ligands.

Typically, bidentate diphosphine compounds are used here as ligands. A very good catalytic system was developed by Lucite now Mitsubishi Rayon and uses a ligand based on 1,2-bis(di-tert-butylphosphinomethyl)benzene (DTBPMB) (W. Clegg, G. R. Eastham, M. R. J. Elsegood, R. P. Tooze, X. L. Wang, K. Whiston, Chem. Commun. 1999, 1877-1878).

The problem addressed by the present invention is that of providing novel ligands for alkoxycarbonylation, with which higher yields of esters can be achieved. More particularly, the ligands according to the invention are to be suitable for the alkoxycarbonylation of long-chain ethylenically unsaturated compounds, for example $C_8$ olefins, and of mixtures of ethylenically unsaturated compounds. The presence of functional groups is also tolerated.

This problem is solved by benzene-based diphosphine compounds substituted by at least one heteroaryl radical on at least one phosphorus atom. These compounds are particularly suitable as bidentate ligands for palladium complexes and lead to elevated yields in the alkoxycarbonylation of a multitude of different ethylenically unsaturated compounds. The ligands according to the invention also lead to lower formation of ethers as by-products and improve the n/iso selectivity of the alkoxycarbonylation.

The diphosphine compounds according to the invention are compounds of formula (I)

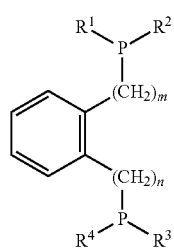

(I)

where
m and n are each independently 0 or 1;
$R^1$, $R^2$, $R^3$, $R^4$ are each independently selected from —$(C_1$-$C_{12})$-alkyl, —$(C_3$-$C_{12})$-cycloalkyl, —$(C_3$-$C_{12})$-heterocycloalkyl, —$(C_6$-$C_{20})$-aryl, —$(C_3$-$C_{20})$-heteroaryl;
at least one of the $R^1$, $R^2$, $R^3$, $R^4$ radicals is a —$(C_3$-$C_{20})$-heteroaryl radical; and
$R^1$, $R^2$, $R^3$, $R^4$, if they are —$(C_1$-$C_{12})$-alkyl, —$(C_3$-$C_{12})$-cycloalkyl, —$(C_3$-$C_{12})$-heterocycloalkyl, —$(C_6$-$C_{20})$-aryl or —$(C_3$-$C_{20})$-heteroaryl,
may each independently be substituted by one or more substituents selected from —$(C_1$-$C_{12})$-alkyl, —$(C_3$-$C_{12})$-cycloalkyl, —$(C_3$-$C_{12})$-heterocycloalkyl, —O—$(C_1$-$C_{12})$-alkyl, —O—$(C_1$-$C_{12})$-alkyl-$(C_6$-$C_{20})$-aryl, —O—$(C_3$-$C_{12})$-cycloalkyl, —S—$(C_1$-$C_{12})$-alkyl, —S—$(C_3$-$C_{12})$-cycloalkyl, —COO—$(C_1$-$C_{12})$-alkyl, —COO—$(C_3$-$C_{12})$-cycloalkyl, —CONH—$(C_1$-$C_{12})$-alkyl, —CONH—$(C_3$-$C_{12})$-cycloalkyl, —CO—$(C_1$-$C_{12})$-alkyl, —CO—$(C_3$-$C_{12})$-cycloalkyl, —N—[$(C_1$-$C_{12})$-alkyl]$_2$, —$(C_6$-$C_{20})$-aryl, —$(C_6$-$C_{20})$-aryl-$(C_1$-$C_{12})$-alkyl, —$(C_6$-$C_{20})$-aryl-O—$(C_1$-$C_{12})$-alkyl, —$(C_3$-$C_{20})$-heteroaryl, —$(C_3$-$C_{20})$-heteroaryl-$(C_1$-$C_{12})$-alkyl, —$(C_3$-$C_{20})$-heteroaryl-O—$(C_1$-$C_{12})$-alkyl, —COOH, —OH, —$SO_3H$, —$NH_2$, halogen.

In one embodiment, the diphosphine compounds according to the invention are compounds of one of the formulae (II) and (III)

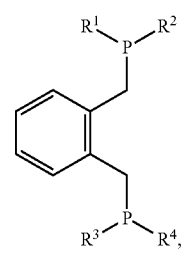

(II)

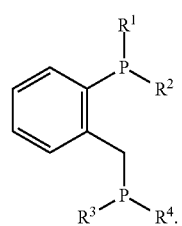

(III)

In these formulae, the $R^1$, $R^2$, $R^3$, $R^4$ radicals are each as defined above.

The expression $(C_1$-$C_{12})$-alkyl encompasses straight-chain and branched alkyl groups having 1 to 12 carbon atoms. These are preferably $(C_1$-$C_8)$-alkyl groups, more preferably $(C_1$-$C_6)$-alkyl, most preferably $(C_1$-$C_4)$-alkyl.

Suitable $(C_1$-$C_{12})$-alkyl groups are especially methyl, ethyl, propyl, isopropyl, n-butyl, iso-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The elucidations relating to the expression $(C_1-C_{12})$-alkyl also apply particularly to the alkyl groups in —O—$(C_1-C_{12})$-alkyl, —S—$(C_1-C_{12})$-alkyl, —COO—$(C_1-C_{12})$-alkyl, —CONH—$(C_1-C_{12})$-alkyl, —CO—$(C_1-C_{12})$-alkyl and —N—$[(C_1-C_{12})$-alkyl$]_2$.

The expression $(C_3-C_{12})$-cycloalkyl encompasses mono-, bi- or tricyclic hydrocarbyl groups having 3 to 12 carbon atoms. Preferably, these groups are $(C_5-C_{12})$-cycloalkyl.

The $(C_3-C_{12})$-cycloalkyl groups have preferably 3 to 8, more preferably 5 or 6, ring atoms.

Suitable $(C_3-C_{12})$-cycloalkyl groups are especially cyclopropyl, cyclobutyl, cyclopentyl, cyclohexyl, cycloheptyl, cyclooctyl, cyclododecyl, cyclopentadecyl, norbornyl, adamantyl.

The elucidations relating to the expression $(C_3-C_{12})$-cycloalkyl also apply particularly to the cycloalkyl groups in —O—$(C_3-C_{12})$-cycloalkyl, —S—$(C_3-C_{12})$-cycloalkyl, —COO—$(C_3-C_{12})$-cycloalkyl, —CONH—$(C_3-C_{12})$-cycloalkyl, —CO—$(C_3-C_{12})$-cycloalkyl.

The expression $(C_3-C_{12})$-heterocycloalkyl encompasses nonaromatic, saturated or partly unsaturated cycloaliphatic groups having 3 to 12 carbon atoms, where one or more of the ring carbon atoms are replaced by heteroatoms. The $(C_3-C_{12})$-heterocycloalkyl groups have preferably 3 to 8, more preferably 5 or 6, ring atoms and are optionally substituted by aliphatic side chains. In the heterocycloalkyl groups, as opposed to the cycloalkyl groups, one or more of the ring carbon atoms are replaced by heteroatoms or heteroatom-containing groups. The heteroatoms or the heteroatom-containing groups are preferably selected from O, S, N, N(=O), C(=O), S(=O). A $(C_3-C_{12})$-heterocycloalkyl group in the context of this invention is thus also ethylene oxide.

Suitable $(C_3-C_{12})$-heterocycloalkyl groups are especially tetrahydrothiophenyl, tetrahydrofuryl, tetrahydropyranyl and dioxanyl.

The expression $(C_6-C_{20})$-aryl encompasses mono- or polycyclic aromatic hydrocarbyl radicals having 6 to 20 carbon atoms. These are preferably $(C_6-C_{14})$-aryl, more preferably $(C_6-C_{10})$-aryl.

Suitable $(C_6-C_{20})$-aryl groups are especially phenyl, naphthyl, indenyl, fluorenyl, anthracenyl, phenanthrenyl, naphthacenyl, chrysenyl, pyrenyl, coronenyl. Preferred $(C_6-C_{20})$-aryl groups are phenyl, naphthyl and anthracenyl.

The expression $(C_3-C_{20})$-heteroaryl encompasses mono- or polycyclic aromatic hydrocarbyl radicals having 3 to 20 carbon atoms, where one or more of the carbon atoms are replaced by heteroatoms. Preferred heteroatoms are N, O and S. The $(C_3-C_{20})$-heteroaryl groups have 3 to 20, preferably 6 to 14 and more preferably 6 to 10 ring atoms. Thus, for example, pyridyl in the context of this invention is a $C_6$-heteroaryl radical; furyl is a $C_5$-heteroaryl radical.

Suitable $(C_3-C_{20})$-heteroaryl groups are especially furyl, thienyl, pyrrolyl, oxazolyl, isoxazolyl, thiazolyl, isothiazolyl, imidazolyl, pyrazolyl, furazanyl, tetrazolyl, pyridyl, pyridazinyl, pyrimidyl, pyrazinyl, benzofuranyl, indolyl, isoindolyl, benzimidazolyl, quinolyl, isoquinolyl.

The expression halogen especially encompasses fluorine, chlorine, bromine and iodine. Particular preference is given to fluorine and chlorine.

In one embodiment, the $R^1$, $R^2$, $R^3$, $R^4$ radicals, if they are —$(C_1-C_{12})$-alkyl, —$(C_3-C_{12})$-cycloalkyl, —$(C_3-C_{12})$-heterocycloalkyl, —$(C_6-C_{20})$-aryl, or —$(C_3-C_{20})$-heteroaryl, may each independently be substituted by one or more substituents selected from —$(C_1-C_{12})$-alkyl, —$(C_3-C_{12})$-cycloalkyl, —$(C_3-C_{12})$-heterocycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —S—$(C_1-C_{12})$-alkyl, —S—$(C_3-C_{12})$-cycloalkyl, —$(C_6-C_{20})$-aryl, —$(C_6-C_{20})$-aryl-$(C_1-C_{12})$-alkyl, —$(C_6-C_{20})$-aryl-O—$(C_1-C_{12})$-alkyl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl, —COOH, —OH, —$SO_3H$, —$NH_2$, halogen.

In one embodiment, the $R^1$, $R^2$, $R^3$, $R^4$ radicals, if they are —$(C_1-C_{12})$-alkyl, —$(C_3-C_{12})$-cycloalkyl, —$(C_3-C_{12})$-heterocycloalkyl, —$(C_6-C_{20})$-aryl, or —$(C_3-C_{20})$-heteroaryl, may each independently be substituted by one or more substituents selected from —$(C_1-C_{12})$-alkyl, —$(C_3-C_{12})$-cycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —$(C_6-C_{20})$-aryl, —$(C_6-C_{20})$-aryl-$(C_1-C_{12})$-alkyl, —$(C_6-C_{20})$-aryl-O—$(C_1-C_{12})$-alkyl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl.

In one embodiment, the $R^1$, $R^2$, $R^3$, $R^4$ radicals, if they are —$(C_1-C_{12})$-alkyl, —$(C_3-C_{12})$-cycloalkyl, —$(C_3-C_{12})$-heterocycloalkyl, —$(C_6-C_{20})$-aryl, or —$(C_3-C_{20})$-heteroaryl, may each independently be substituted by one or more substituents selected from —$(C_1-C_{12})$-alkyl, —O—$(C_1-C_{12})$-alkyl-$(C_6-C_{20})$-aryl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl.

In one embodiment, the $R^1$, $R^2$, $R^3$, $R^4$ radicals, if they are —$(C_1-C_{12})$-alkyl, —$(C_3-C_{12})$-cycloalkyl, —$(C_3-C_{12})$-heterocycloalkyl, —$(C_6-C_{20})$-aryl, or —$(C_3-C_{20})$-heteroaryl, may each independently be substituted by one or more substituents selected from —$(C_1-C_{12})$-alkyl and —$(C_3-C_{20})$-heteroaryl.

In one embodiment, the $R^1$, $R^2$, $R^3$, $R^4$ radicals are unsubstituted if they are —$(C_1-C_{12})$-alkyl, —$(C_3-C_{12})$-cycloalkyl, or —$(C_3-C_{12})$-heterocycloalkyl, and may be substituted as described if they are —$(C_6-C_{20})$-aryl, or —$(C_3-C_{20})$-heteroaryl.

In one embodiment, the $R^1$, $R^2$, $R^3$, $R^4$ radicals are unsubstituted if they are —$(C_1-C_{12})$-alkyl, —$(C_3-C_{12})$-cycloalkyl, —$(C_3-C_{12})$-heterocycloalkyl, —$(C_6-C_{20})$-aryl, or —$(C_3-C_{20})$-heteroaryl.

In one embodiment, $R^1$, $R^2$, $R^3$, $R^4$ are each independently selected from —$(C_1-C_{12})$-alkyl, —$(C_6-C_{20})$-aryl, —$(C_3-C_{20})$-heteroaryl;

where at least one of the $R^1$, $R^2$, $R^3$, $R^4$ radicals is a —$(C_3-C_{20})$-heteroaryl radical;

and $R^1$, $R^2$, $R^3$, $R^4$, if they are —$(C_1-C_{12})$-alkyl, —$(C_6-C_{20})$-aryl or —$(C_3-C_{20})$-heteroaryl, may each independently be substituted by one or more of the above-described substituents.

In one embodiment, at least two of the $R^1$, $R^2$, $R^3$, $R^4$ radicals are a —$(C_3-C_{20})$-heteroaryl radical.

In one embodiment, the $R^1$ and $R^3$ radicals are each a —$(C_3-C_{20})$-heteroaryl radical and may each independently be substituted by one or more of the substituents described above. Preferably, $R^2$ and $R^4$ are independently selected from —$(C_1-C_{12})$-alkyl, —$(C_3-C_{12})$-cycloalkyl, —$(C_3-C_{12})$-heterocycloalkyl, —$(C_6-C_{20})$-aryl, more preferably from —$(C_1-C_{12})$-alkyl, —$(C_3-C_{12})$-cycloalkyl, —$(C_6-C_{20})$-aryl, most preferably from —$(C_1-C_{12})$-alkyl. $R^2$ and $R^4$ may independently be substituted by one or more of the above-described substituents.

In one embodiment, the $R^1$, $R^2$, $R^3$ and $R^4$ radicals are a —$(C_6-C_{20})$-heteroaryl radical and may each independently be substituted by one or more of the substituents described above.

In one embodiment, the $R^1$, $R^2$, $R^3$ and $R^4$ radicals, if they are a heteroaryl radical, are each independently selected from heteroaryl radicals having five to ten ring atoms, preferably five or six ring atoms.

In one embodiment, the $R^1$, $R^2$, $R^3$ and $R^4$ radicals, if they are a heteroaryl radical, are a heteroaryl radical having five ring atoms.

In one embodiment, the $R^1$, $R^2$, $R^3$ and $R^4$ radicals, if they are a heteroaryl radical, are each independently selected from heteroaryl radicals having six to ten ring atoms.

In one embodiment, the $R^1$, $R^2$, $R^3$ and $R^4$ radicals, if they are a heteroaryl radical, are a heteroaryl radical having six ring atoms.

In one embodiment, the $R^1$, $R^2$, $R^3$ and $R^4$ radicals, if they are a heteroaryl radical, are selected from furyl, thienyl, pyrrolyl, oxazolyl, isoxazolyl, thiazolyl, isothiazolyl, imidazolyl, pyrazolyl, furazanyl, tetrazolyl, pyridyl, pyridazinyl, pyrimidyl, pyrazinyl, benzofuranyl, indolyl, isoindolyl, benzimidazolyl, quinolyl, isoquinolyl, where the heteroaryl radicals mentioned may be substituted as described above.

In one embodiment, the $R^1$, $R^2$, $R^3$ and $R^4$ radicals, if they are a heteroaryl radical, are selected from furyl, thienyl, pyrrolyl, imidazolyl, pyridyl, pyrimidyl, indolyl, where the heteroaryl radicals mentioned may be substituted as described above.

In one embodiment, the $R^1$, $R^2$, $R^3$ and $R^4$ radicals, if they are a heteroaryl radical, are selected from 2-furyl, 2-thienyl, 2-pyrrolyl, 2-imidazolyl, 2-pyridyl, 2-pyrimidyl, 2-indolyl, where the heteroaryl radicals mentioned may be substituted as described above.

In one embodiment, the $R^1$, $R^2$, $R^3$ and $R^4$ radicals, if they are a heteroaryl radical, are selected from 2-furyl, 2-thienyl, N-methyl-2-pyrrolyl, N-phenyl-2-pyrrolyl, N-(2-methoxyphenyl)-2-pyrrolyl, 2-pyrrolyl, N-methyl-2-imidazolyl, 2-imidazolyl, 2-pyridyl, 2-pyrimidyl, N-phenyl-2-indolyl, 2-indolyl, where the heteroaryl radicals mentioned have no further substitution.

More preferably, the $R^1$, $R^2$, $R^3$ and $R^4$ radicals, if they are a heteroaryl radical, are pyridyl, especially 2-pyridyl.

In one embodiment, $R^1$ and $R^3$ are a pyridyl radical, preferably 2-pyridyl, and $R^2$ and $R^4$ are —($C_1$-$C_{12}$)-alkyl, where $R^1$, $R^2$, $R^3$ and $R^4$ may each be substituted as described above.

In one embodiment, the diphosphine compounds according to the invention are selected from one of the formulae (1) and (18):

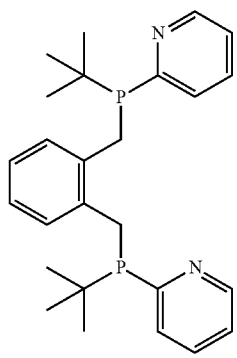

(1)

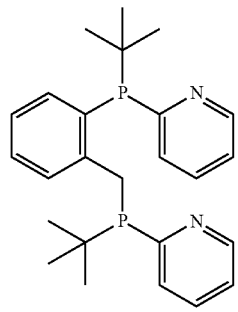

(18)

The invention further relates to complexes comprising Pd and a diphosphine compound according to the invention. In these complexes, the diphosphine compound according to the invention serves as a bidentate ligand for the metal atom. The complexes serve, for example, as catalysts for alkoxycarbonylation. With the complexes according to the invention, it is possible to achieve high yields in the alkoxycarbonylation of a multitude of different ethylenically unsaturated compounds.

The complexes according to the invention may also comprise further ligands which coordinate to the metal atom. These are, for example, ethylenically unsaturated compounds or anions. Suitable additional ligands are, for example, styrene, maleimides (e.g. N-methylmaleimide), 1,4-naphthoquinone, acetate anions, trifluoroacetate anions or chloride anions.

The invention further relates to the use of a diphosphine compound according to the invention for catalysis of an alkoxycarbonylation reaction. The compound according to the invention can especially be used as a metal complex according to the invention.

The invention also relates to a process comprising the process steps of:
a) initially charging an ethylenically unsaturated compound;
b) adding a diphosphine compound according to the invention and a compound comprising Pd, or adding a complex according to the invention comprising Pd and a diphosphine compound according to the invention;
c) adding an alcohol;
d) feeding in CO;
e) heating the reaction mixture, with conversion of the ethylenically unsaturated compound to an ester.

In this process, process steps a), b), c) and d) can be effected in any desired sequence. Typically, however, the addition of CO is effected after the co-reactants have been initially charged in steps a) to c). Steps d) and e) can be effected simultaneously or successively. In addition, CO can also be fed in two or more steps, in such a way that, for example, a portion of the CO is first fed in, then the mixture is heated, and then a further portion of CO is fed in.

The ethylenically unsaturated compounds used as reactant in the process according to the invention contain one or more carbon-carbon double bonds. These compounds are also referred to hereinafter as olefins for simplification. The double bonds may be terminal or internal.

Preference is given to ethylenically unsaturated compounds having 2 to 30 carbon atoms, preferably 2 to 22 carbon atoms, more preferably 2 to 12 carbon atoms.

In one embodiment, the ethylenically unsaturated compound comprises 2 to 30 carbon atoms, preferably 6 to 22 carbon atoms, more preferably 8 to 12 carbon atoms, most preferably 8 carbon atoms.

The ethylenically unsaturated compounds may, in addition to the one or more double bonds, contain further functional groups. Preferably, the ethylenically unsaturated compound comprises one or more functional groups selected from carboxyl, thiocarboxyl, sulpho, sulphinyl, carboxylic anhydride, imide, carboxylic ester, sulphonic ester, carbamoyl, sulphamoyl, cyano, carbonyl, carbonothioyl, hydroxyl, sulphhydryl, amino, ether, thioether, aryl, heteroaryl or silyl groups and/or halogen substituents. At the same time, the ethylenically unsaturated compound preferably comprises a total of 2 to 30 carbon atoms, preferably 2 to 22 carbon atoms, more preferably 2 to 12 carbon atoms.

In one embodiment, the ethylenically unsaturated compound does not comprise any further functional groups apart from carbon-carbon double bonds.

In a particularly preferred embodiment, the ethylenically unsaturated compound is an unfunctionalized alkene having at least one double bond and 2 to 30 carbon atoms, preferably 6 to 22 carbon atoms, further preferably 8 to 12 carbon atoms, and most preferably 8 carbon atoms.

Suitable ethylenically unsaturated compounds are, for example:
ethene;
propene;
C4 olefins such as 1-butene, cis-2-butene, trans-2-butene, mixture of cis- and trans-2-butene, isobutene, 1,3-butadiene; raffinate I to III, crack-C4
C5 olefins such as 1-pentene, 2-pentene, 2-methyl-1-butene, 2-methyl-2-butene, 2-methyl-1,3-butadiene (isoprene), 1,3-pentadiene;
C6 olefins such as tetramethylethylene, 1,3-hexadiene, 1,3-cyclohexadiene;
C7 olefins such as 1-methylcyclohexene, 2,4-heptadiene, norbornadiene;
C8 olefins such as 1-octene, 2-octene, cyclooctene, di-n-butene, diisobutene, 1,5-cyclooctadiene, 1,7-octadiene;
C9 olefins such as tripropene;
C10 olefins such as dicyclopentadiene;
undecenes;
dodecenes;
internal C14 olefins;
internal C15 to C18 olefins;
linear or branched, cyclic, acyclic or partly cyclic, internal C15 to C30 olefins;
triisobutene, tri-n-butene;
terpenes such as limonene, geraniol, farnesol, pinene, myrcene, carvone, 3-carene;
polyunsaturated compounds having 18 carbon atoms, such as linoleic acid or linolenic acid;
esters of unsaturated carboxylic acids, such as vinyl esters of acetic or propionic acid, alkyl esters of unsaturated carboxylic acids, methyl or ethyl esters of acrylic acid and methacrylic acid, oleic esters, such as methyl or ethyl oleate, esters of linoleic or linolenic acid; vinyl compounds such as vinyl acetate, vinylcyclohexene, styrene, alpha-methylstyrene, 2-isopropenylnaphthalene;
2-methyl-2-pentenal, methyl 3-pentenoate, methacrylic anhydride.

In one variant of the process, the ethylenically unsaturated compound is selected from propene, 1-butene, cis- and/or trans-2-butene, or mixtures thereof.

In one variant of the process, the ethylenically unsaturated compound is selected from 1-pentene, cis- and/or trans-2-pentene, 2-methyl-1-butene, 2-methyl-2-butene, 3-methyl-1-butene, or mixtures thereof.

In a preferred embodiment, the ethylenically unsaturated compound is selected from ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, n-octene, 1-octene, 2-octene, or mixtures thereof The ethylenically unsaturated compound may additionally be selected from 1,7-octadiene, cyclooctene, methyl 10-undecenoate, 1-methylcyclohexene, 5-hexenenitrile, 6-chloro-1-hexene, vinyltriethylsilane, carvone, isopropenylbenzene, 4-chloroisopropenylbenzene, 4-fluoroisopropenylbenzene, 2-methylisopropenylbenzene, 2-isopropenylnaphthalene, 1,1-diphenylethylene, 1,3-diisopropenylbenzene,

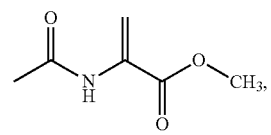

tetramethylethylene, N-vinylphthalimide, 2,3,4,5,6-pentafluorostyrene,

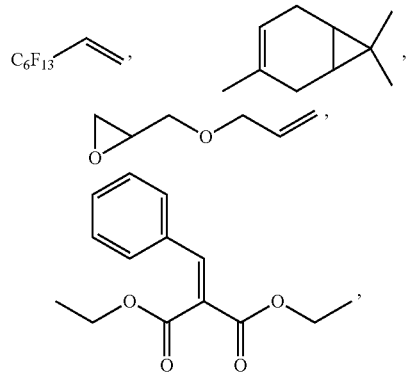

ethyl trans-2-butenoate.

In one variant, a mixture of ethylenically unsaturated compounds is used. A mixture in the context of this invention refers to a composition comprising at least two different ethylenically unsaturated compounds, where the proportion of each individual ethylenically unsaturated compound is preferably at least 5% by weight, based on the total weight of the mixture.

Preference is given to using a mixture of ethylenically unsaturated compounds each having 2 to 30 carbon atoms, preferably 4 to 22 carbon atoms, more preferably 6 to 12 carbon atoms, most preferably 8 to 10 carbon atoms.

Suitable mixtures of ethylenically unsaturated compounds are those called raffinates I to III. Raffinate I comprises 40% to 50% isobutene, 20% to 30% 1-butene, 10% to 20% cis- and trans-2-butene, up to 1% 1,3-butadiene and 10% to 20% n-butane and isobutane. Raffinate II is a portion of the $C_4$ fraction which arises in naphtha cracking and consists essentially of the isomeric n-butenes, isobutane and n-butane after removal of isobutene from raffinate I.

Raffinate III is a portion of the $C_4$ fraction which arises in naphtha cracking and consists essentially of the isomeric n-butenes and n-butane.

A further suitable mixture is di-n-butene, also referred to as dibutene, DNB or DnB. Di-n-butene is an isomer mixture of C8 olefins which arises from the dimerization of mixtures of 1-butene, cis-2-butene and trans-2-butene. In industry, raffinate II or raffinate III streams are generally subjected to a catalytic oligomerization, wherein the butanes present (n/iso) emerge unchanged and the olefins present are converted fully or partly. As well as dimeric di-n-butene, higher oligomers (tributene C12, tetrabutene C16) generally also form, which are removed by distillation after the reaction. These can likewise be used as reactants.

In a preferred variant, a mixture comprising isobutene, 1-butene, cis- and trans-2-butene is used. Preferably, the mixture comprises 1-butene, cis- and trans-2-butene.

The alkoxycarbonylation according to the invention is catalysed by the Pd complex according to the invention. The Pd complex may either be added in process step b) as a preformed complex comprising Pd and the phosphine ligands according to the invention or be formed in situ from a compound comprising Pd and the free phosphine ligand. In this context, the compound comprising Pd is also referred to as catalyst precursor.

In the case that the catalyst is formed in situ, the ligand can be added in excess, such that the unbound ligand is also present in the reaction mixture.

In the case of the complex which is added right at the start as well, it is also possible to add further ligand, such that unbound ligand is also present in the reaction mixture.

In one variant, the compound comprising Pd is selected from palladium chloride ($PdCl_2$), palladium(II) acetylacetonate [$Pd(acac)_2$], palladium(II) acetate [$Pd(OAc)_2$], dichloro (1,5-cyclooctadiene)palladium(II) [$Pd(cod)_2Cl_2$], bis(dibenzylideneacetone)palladium [$Pd(dba)_2$], bis(acetonitrile) dichloropalladium(II) [$Pd(CH_3CN)_2Cl_2$], palladium (cinnamyl) dichloride [$Pd(cinnamyl)Cl_2$].

Preferably, the compound comprising Pd is $PdCl_2$, $Pd(acac)_2$ or $Pd(OAc)_2$. $PdCl_2$ is particularly suitable.

The alcohol in process step c) may be branched or linear, cyclic, alicyclic, partly cyclic or aliphatic, and is especially a $C_1$- to $C_{30}$-alkanol. It is possible to use monoalcohols or polyalcohols.

The alcohol in process step c) comprises preferably 1 to 30 carbon atoms, more preferably 1 to 22 carbon atoms, especially preferably 1 to 12 carbon atoms. It may be a monoalcohol or a polyalcohol.

The alcohol may, in addition to the one or more hydroxyl groups, contain further functional groups. Preferably, the alcohol may additionally comprise one or more functional groups selected from carboxyl, thiocarboxyl, sulpho, sulphinyl, carboxylic anhydride, imide, carboxylic ester, sulphonic ester, carbamoyl, sulphamoyl, cyano, carbonyl, carbonothioyl, sulphhydryl, amino, ether, thioether, aryl, heteroaryl or silyl groups and/or halogen substituents.

In one embodiment, the alcohol does not comprise any further functional groups except for hydroxyl groups.

The alcohol may contain unsaturated and aromatic groups. However, it is preferably an aliphatic alcohol.

An aliphatic alcohol in the context of this invention refers to an alcohol which does not comprise any aromatic groups, i.e., for example, an alkanol, alkenol or alkynol.

In one embodiment, the alcohol is an alkanol having one or more hydroxyl groups and 1 to 30 carbon atoms, preferably 1 to 22 carbon atoms, more preferably 1 to 12 carbon atoms, most preferably 1 to 6 carbon atoms.

In one variant of the process, the alcohol in process step c) is selected from the group of the monoalcohols.

In one variant of the process, the alcohol in process step c) is selected from: methanol, ethanol, 1-propanol, isopropanol, isobutanol, tert-butanol, 1-butanol, 2-butanol, 1-pentanol, 2-pentanol, 3-pentanol, 1-hexanol, cyclohexanol, phenol, 2-ethylhexanol, isononanol, 2-propylheptanol.

In a preferred variant, the alcohol in process step c) is selected from methanol, ethanol, 1-propanol, 1-butanol, 1-pentanol, 1-hexanol, 2-propanol, tert-butanol, 3-pentanol, cyclohexanol, phenol, and mixtures thereof.

In one variant of the process, the alcohol in process step c) is selected from the group of the polyalcohols.

In one variant of the process, the alcohol in process step c) is selected from: diols, triols, tetraols.

In one variant of the process, the alcohol in process step c) is selected from: cyclohexane-1,2-diol, ethane-1,2-diol, propane-1,3-diol, glycerol, butane-1,2,4-triol, 2-hydroxymethylpropane-1,3-diol, 1,2,6-trihydroxyhexane, pentaerythritol, 1,1,1-tri(hydroxymethyl)ethane, catechol, resorcinol and hydroxyhydroquinone.

In one variant of the process, the alcohol in process step c) is selected from: sucrose, fructose, mannose, sorbose, galactose and glucose.

In a preferred embodiment of the process, the alcohol in process step c) is selected from methanol, ethanol, 1-propanol, 1-butanol, 1-pentanol, 1-hexanol.

In a particularly preferred variant of the process, the alcohol in process step c) is selected from: methanol, ethanol.

In a particularly preferred variant of the process, the alcohol in process step c) is methanol.

In one variant of the process, the alcohol in process step c) is used in excess.

In one variant of the process, the alcohol in process step c) is used simultaneously as solvent.

In one variant of the process, a further solvent is used, selected from: toluene, xylene, tetrahydrofuran (THF) and methylene chloride ($CH_2Cl_2$).

CO is fed in step d) preferably at a partial CO pressure between 0.1 and 10 MPa (1 to 100 bar), preferably between 1 and 8 MPa (10 to 80 bar), more preferably between 2 and 4 MPa (20 to 40 bar).

The reaction mixture is heated in step e) of the process according to the invention preferably to a temperature between 10° C. and 180° C., preferably between 20 and 160° C., more preferably between 40 and 120° C., in order to convert the ethylenically unsaturated compound to an ester.

The molar ratio of the ethylenically unsaturated compound initially charged in step a) to the alcohol added in step c) is preferably between 1:1 and 1:20, more preferably 1:2 to 1:10, more preferably 1:3 to 1:4.

The mass ratio of Pd to the ethylenically unsaturated compound initially charged in step a) is preferably between 0.001% and 0.5% by weight, preferably between 0.01% and 0.1% by weight, more preferably between 0.01% and 0.05% by weight.

The molar ratio of the diphosphine compound according to the invention to Pd is preferably between 0.1:1 and 400:1, preferably between 0.5:1 and 400:1, more preferably between 1:1 and 100:1, most preferably between 2:1 and 50:1.

Preferably, the process is conducted with addition of an acid. In one variant, the process therefore additionally comprises step c'): adding an acid to the reaction mixture. This may preferably be a Brønsted or Lewis acid.

Suitable Brønsted acids preferably have an acid strength of $pK_a \leq 5$, preferably an acid strength of $pK_a \leq 3$. The reported acid strength $pK_a$ is based on the $pK_a$ determined under standard conditions (25° C., 1.01325 bar). In the case of a polyprotic acid, the acid strength $pK_a$ in the context of this invention relates to the $pK_a$ of the first protolysis step.

Preferably, the acid is not a carboxylic acid.

Suitable Brønsted acids are, for example, perchloric acid, sulphuric acid, phosphoric acid, methylphosphonic acid and sulphonic acids. Preferably, the acid is sulphuric acid or a sulphonic acid. Suitable sulphonic acids are, for example, methanesulphonic acid, trifluoromethanesulphonic acid, tert-butanesulphonic acid, p-toluenesulphonic acid (PTSA), 2-hydroxypropane-2-sulphonic acid, 2,4,6-trimethylbenzenesulphonic acid and dodecylsulphonic acid. Particularly preferred acids are sulphuric acid, methanesulphonic acid, trifluoromethanesulphonic acid and p-toluenesulphonic acid.

A Lewis acid used may, for example, be aluminium triflate.

In one embodiment, the amount of acid added in step c') is 0.3 to 40 mol %, preferably 0.4 to 15 mol %, more preferably 0.5 to 5 mol %, most preferably 0.6 to 3 mol %, based on the molar amount of the ethylenically unsaturated compound used in step a).

DESCRIPTION OF ILLUSTRATIONS

FIG. 1: Methoxycarbonylation of di-n-butene with ligand 1 at 120° C. and 40 bar.

Figure 2:
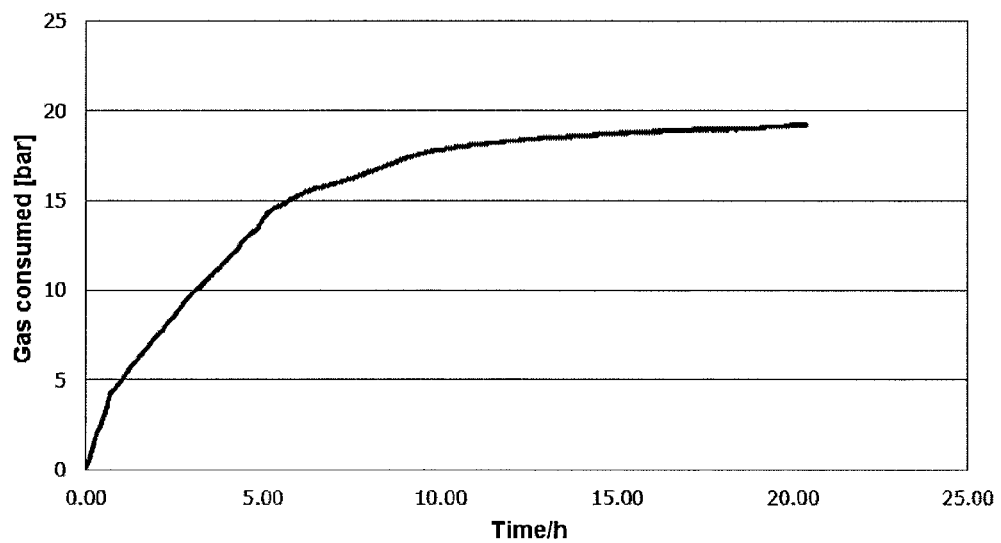

FIG. 2: Methoxycarbonylation of di-n-butene with ligand 1 at 100° C. and 12 bar.

EXAMPLES

The examples which follow illustrate the invention.

General Procedures

All the preparations which follow were carried out under protective gas using standard Schlenk techniques. The solvents were dried over suitable desiccants before use (Purification of Laboratory Chemicals, W. L. F. Armarego (Author), Christina Chai (Author), Butterworth Heinemann (Elsevier), 6th edition, Oxford 2009).

Phosphorus trichloride (Aldrich) was distilled under argon before use. All preparative operations were effected in baked-out vessels. The products were characterized by means of NMR spectroscopy. Chemical shifts (δ) are reported in ppm. The $^{31}$P NMR signals were referenced as follows: $SR_{31P} = SR_{1H}*(BF_{31P}/BF_{1H}) = SR_{1H}*0.4048$. (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E. Hoffman and Kurt W. Zilm, Pure Appl. Chem., 2008, 80, 59-84).

The recording of nuclear resonance spectra was effected on Bruker Avance 300 or Bruker Avance 400, gas chromatography analysis on Agilent GC 7890A, elemental analysis on Leco TruSpec CHNS and Varian ICP-OES 715, and ESI-TOF mass spectrometry on Thermo Electron Finnigan MAT 95-XP and Agilent 6890 N/5973 instruments.

Preparation of chloro-2-pyridyl-tert-butylphosphine (precursor A)

The Grignard for the synthesis of chloro-2-pyridyl-t-butylphosphine is prepared by the "Knochel method" with isopropylmagnesium chloride (Angew. Chem. 2004, 43, 2222-2226). The workup is effected according to the method of Budzelaar (Organometallics 1990, 9, 1222-1227).

Scheme 1: Synthesis of precursor A

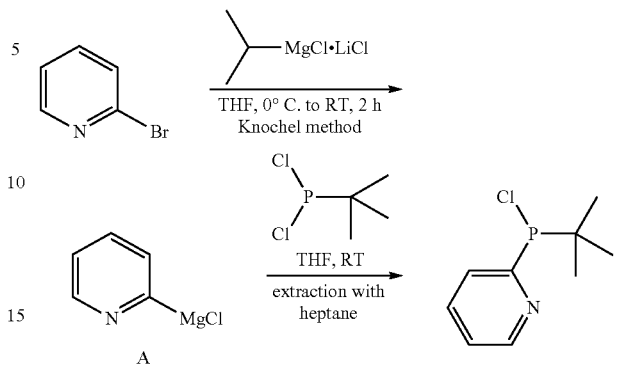

8.07 ml of a 1.3 M isopropylmagnesium chloride solution (Knochel's reagent) are introduced into a 50 ml round-bottom flask with magnetic stirrer and septum, and cooled to −15° C. Thereafter, 953.5 μl (10 mmol) of 2-bromopyridine are rapidly added dropwise. The solution immediately turns yellow. It is allowed to warm up to −10° C. The conversion of the reaction is determined as follows: about 100 μl solution are taken and introduced into 1 ml of a saturated ammonium chloride solution. If the solution "bubbles", not much Grignard has formed yet. The aqueous solution is extracted with a pipette of ether and the organic phase is dried over $Na_2SO_4$. A GC of the ethereal solution is recorded. When a large amount of pyridine has formed compared to 2-bromopyridine, conversions are high. At −10° C., there has been little conversion. After warming up to room temperature and stirring for 1-2 hours, the reaction solution turns brown-yellow. A GC test shows complete conversion. Now the Grignard solution can be slowly added dropwise with a syringe pump to a solution of 1.748 g (11 mmol) of dichloro-tert-butylphosphine in 10 ml of THF which has been cooled to −15° C. beforehand. It is important that the dichloro-tert-butylphosphine solution is cooled. At room temperature, considerable amounts of dipyridyl-tert-butylphosphine would be obtained. A clear yellow solution is initially formed, which then turns cloudy. The mixture is left to warm up to room temperature and to stir overnight. According to GC-MS, a large amount of product has formed. The solvent is removed under high vacuum and a whitish solid which is brown in places is obtained. The solid is suspended with 20 ml of heptane and the solid is comminuted in an ultrasound bath. After allowing the white solid to settle out, the solution is decanted. The operation is repeated twice with 10-20 ml each time of heptane. After concentration of the heptane solution under high vacuum, it is distilled under reduced pressure. At 4.6 mbar, oil bath 120° C. and distillation temperature 98° C., the product can be distilled. 1.08 g of a colourless oil are obtained. (50%).

Analytical data: $^1$H NMR (300 MHz, $C_6D_6$): δ 8.36 (m, 1H, Py), 7.67 (m, 1H, Py), 7.03-6.93 (m, 1H, Py), 6.55-6.46 (m, 1H, Py), 1.07 (d, J=13.3 Hz, 9H, t-Bu).

$^{13}$C NMR (75 MHz, $C_6D_6$): δ 162.9, 162.6, 148.8, 135.5, 125.8, 125.7, 122.8, 35.3, 34.8, 25.9 and 25.8.

$^{31}$P NMR (121 MHz, $C_6D_6$) δ 97.9.

MS (EI) m:z (relative intensity) 201 (M$^+$,2), 147(32), 145 (100), 109 (17), 78 (8), 57.1 (17).

Preparation of compound 1 (α,α'-bis(2-pyridyl(t-butyl)phosphino)o-xylene)

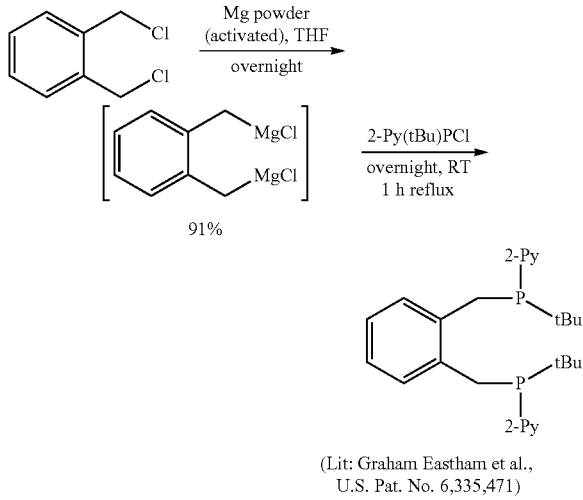

Scheme 2: Synthesis of compound 1

(Lit: Graham Eastham et al., U.S. Pat. No. 6,335,471)

675 mg (27.8 mmol, 4 eq) of Mg powder are weighed out in a glovebox in a 250 ml round-bottom flask with a nitrogen tap and magnetic stirrer bar, and the flask is sealed with a septum. High vacuum is applied to the round-bottom flask (about $5\times10^{-2}$ mbar) and it is heated to 90° C. for 45 minutes. After cooling down to room temperature, 2 grains of iodine are added and the mixture is dissolved in 20 ml of THF. The suspension is stirred for about 10 minutes until the yellow colour of the iodine has disappeared. After the magnesium powder has settled out, the cloudy THF solution is decanted and the activated magnesium powder is washed twice with 1-2 ml of THF. Then another 20 ml of fresh THF are added. At room temperature, a solution of 1.21 g (6.9 mmol) of α,α'-dichloro-o-xylene in 70 ml of THF is slowly added dropwise with a syringe pump. The THF solution gradually turns a darker colour. The next day, the THF suspension is filtered to remove the unconverted magnesium powder and the content of Grignard compound is determined as follows:

1 ml of Grignard solution is quenched in a saturated aqueous solution of $NH_4Cl$ and extracted with ether. After drying over $Na_2SO_4$, a GC of the ether solution is recorded. In qualitative terms, it is observed that exclusively o-xylene has formed.

Quantitative Determination of the Content of the Grignard Solution:

1 ml of Grignard solution is quenched with 2 ml of 0.1 M HCl and the excess acid is titrated with 0.1 M NaOH. A suitable indicator is an aqueous 0.04% bromocresol solution. The colour change goes from yellow to blue. 0.74 ml of 0.1 M NaOH has been consumed. 2 ml-0.74 ml=1.26 ml, corresponding to 0.126 mmol of Grignard compound. Since a di-Grignard is present, the Grignard solution is 0.063 M. This is a yield exceeding 90%.

In a 250 ml three-neck flask with reflux condenser and magnetic stirrer, under argon, 1.8 g (8.66 mmol) of chlorophosphine (2-Py(tBu)PCl) are dissolved in 10 ml of THF and cooled to −60° C. Then 55 ml of the above-stipulated Grignard solution (0.063 M, 3.46 mmol) are slowly added dropwise at this temperature with a syringe pump. The solution at first remains clear and then turns intense yellow. After 1.5 hours, the solution turns cloudy. The mixture is left to warm up to room temperature overnight and a clear yellow solution is obtained. To complete the reaction, the mixture is heated under reflux for 1 hour. After cooling, 1 ml of $H_2O$ is added and the solution loses colour and turns milky white. After removing THF under high vacuum, a stringy, pale yellow solid is obtained. 10 ml of water and 10 ml of ether are added thereto, and two homogeneous clear phases are obtained, which have good separability. The aqueous phase is extracted twice with ether. After the organic phase has been dried with $Na_2SO_4$, the ether is removed under high vacuum and a stringy, almost colourless solid is obtained. The latter is dissolved in 5 ml of MeOH while heating on a water bath and filtered through Celite. At −28° C., 772 mg of product are obtained in the form of white crystals overnight. (51%). After concentration, it was possible to isolate another 100 mg from the mother solution. The overall yield is 57.6%.

$^1$H NMR (300 MHz, $C_6D_6$): δ 8.58 (m, 2H, Py), 7.31-7.30 (m, 2H, benzene), 7.30-7.22 (m, 2H, Py), 6.85-6.77 (m, 2H, Py), 6.73 (m, 2H, benzene), 6.57-6.50 (m, 2H, py), 4.33 (dd, J=13.3 and 4.3 Hz, 2H, $CH_2$), 3.72-3.62 (m, 2H, $CH_2$), 121 (d, J=11.8 Hz, 18H, tBu), $^{13}$C NMR (75 MHz, $C_6D_6$): δ 161.3, 161.1, 149.6, 137.8, 137.7, 134.5, 133.3, 132.7, 131.4, 131.3, 125.7, 122.9, 30.7, 30.5, 28.2, 28.0, 26.5, 26.4, 26.2, and 26.1.

$^{31}$P NMR (121 MHz, $C_6D_6$) δ 8.8, EA calculated for $C_{26}H_{34}N_2P_2$: C, 71.54; H, 7.85; N, 6.56; P, 14.35. found: C, 71.21; H, 7.55; N, 6.56; P, 14.35.

Preparation of compound 18 (1-(2-pyridyl(t-butyl)phosphino)-2-(2-pyridyl(t-butyl) phosphinomethyl) benzene)

Scheme 3: Synthesis of compound 18

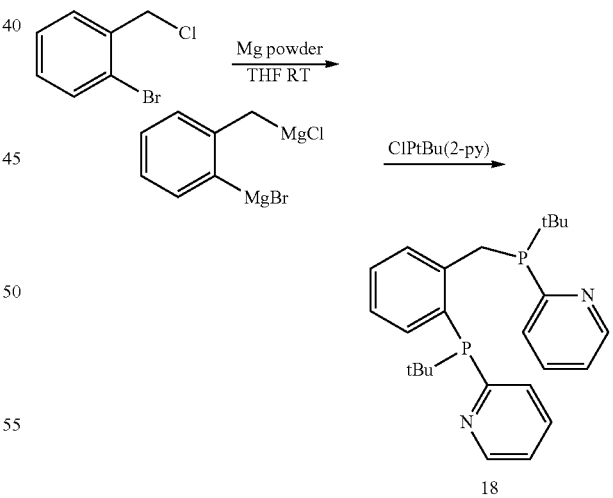

675 mg (27.8 mmol, 4 eq) of Mg powder are weighed into a 250 ml round-bottom flask with a nitrogen tap and magnetic stirrer bar in a glovebox, and the flask is sealed with a septum. High vacuum is applied to the round-bottom flask (about $5\times10^{-2}$ mbar) and it is heated to 90° C. for 45 minutes. After cooling down to room temperature, 2 grains of iodine are added and the mixture is dissolved in 20 ml of THF. The suspension is stirred for about 10 minutes until the yellow colour of the iodine has disappeared. After the magnesium powder has settled out, the cloudy THF solution is decanted and the activated magnesium powder is washed twice with 1-2 ml of THF. Then another 20 ml of fresh THF are added. At room temperature, a solution of 920.7 µl (6.9 mmol) of 2-bromobenzyl chloride in 70 ml of THF is slowly added dropwise with a syringe pump. The THF solution turns cloudy and slightly greenish. The next day, a greenish, milky suspension is present. After allowing the excess Mg powder to settle out, the suspension is decanted and the content of Grignard compound is determined.

1 ml of Grignard solution is quenched with 2 ml of 0.1 M HCl and the excess acid is titrated with 0.1 M NaOH. A suitable indicator is an aqueous 0.04% bromocresol solution. The colour change goes from yellow to blue. 0.4 ml of 0.1 M NaOH has been consumed. 2 ml-0.4 ml=1.6 ml, corresponding to 0.15 mmol of Grignard compound. Since a di-Grignard is present, the Grignard solution is 0.075 M.

In a 250 ml three-neck flask with reflux condenser, under argon, 2.64 g (13.12 mol, 2.5 eq) of chlorophosphine (2-Py (tBu)PCl) are dissolved in 15 ml of THF and cooled to −60° C. Then 70 ml of the milky-greenish Grignard solution (0.075 M, 5.25 mmol) are slowly added dropwise at this temperature with a syringe pump. Over the three hours of dropwise addition, no significant change in the reaction solution is visible. The mixture is left to warm up to room temperature overnight and a clear, dark yellow solution is obtained. To complete the reaction, the mixture is heated under reflux for 2 hours. After cooling, 1 ml of $H_2O$ is added thereto and the THF is removed under high vacuum. A stringy yellowish solid is obtained. Thereafter, 20 ml of water and 30 ml of ether are added thereto, and an inhomogeneous solution having poor phase separation is obtained. By adding absolute methanol, it is possible to accelerate the phase separation. The aqueous phase is extracted twice with ether. The combined ether phase is clear and yellow. After drawing off the ether, 2.1 g of a pale orange crude product are obtained. The latter cannot be crystallized from methanol. To purify the product, the phosphine is converted to the corresponding borane adduct:

the crude product is dissolved in 15 ml THF, and 11.55 ml (2.3 eq) of 1 M borane/THF complex are added all at once. The mixture is left to stir at room temperature for one day and the borane adduct is chromatographed with a Combi-Flash apparatus (ethyl acetate/heptane=1:10). 1.18 g (52%) of a white, porous solid are obtained. It is apparent from the spectra that 2 diastereomers must be present:

$^1$H NMR (400 MHz, CDCl$_3$): δ 8.76 and 8.73 (m, 2H, arom), 8.10 (m, 1H, arom), 7.92-7.62 (m, 3H, arom), 7.40 (m, 2H, arom), 7.31 (m, 1H, arom), 4.22-3.92 (m, 2H, CH$_2$), 1.51 (d, J=14.5 Hz, tBu, 3H), 1.45 (d, J=14.5 Hz, tBu, 6H), 1.23 (d, J=14.5 Hz, 3H, tBu), 1.22 (d, J=14.5 Hz, tBu, 6H).

$^{31}$P NMR (161 MHz, CDCl$_3$) δ 37.71 (d, broad, J=52.8 Hz), 36.52 (d, broad, J=52.9 Hz), 33.65 (s, broad), 31.90 (s, broad).

In order to obtain the free phosphine, the borane adduct is dissolved in 20 ml of morpholine and heated to 50° C. for 4 hours. Thereafter, the morpholine is removed under high vacuum and the residue is chromatographed under argon. (Ethyl acetate/heptane=1:2). The product runs off the column at the front and can thus be isolated easily. The solvent is removed again, and 1.1 g (98%) of a colourless viscous oil are obtained. In the spectrum, two diastereomers again are observed in a ratio of 1:2.

$^1$H NMR (300 MHz, C$_6$D$_6$): δ 8.65, 8.57 and 8.51 (m, 2H, arom), 7.58 and 7.51-7.33 (m, 4H, arom), 7.01 and 7.02-6.76 (m, 4H, arom), 6.63-6.45 (m, 2H, arom), 4.84, 4.47, 4.23 and 3.80 (m, 2H, CH$_2$), 1.53 (d, J=12.8 Hz, 3H, tBu), 1.51 (d, J=12.8 Hz, 6H, tBu), 1.27-1.15 (m, 9H, tBu).

$^{13}$C NMR (75 MHz, C$_6$D$_6$): δ 167.2, 167.0, 149.7, 149.2, 149.0, 148.9, 137.1, 136.7, 136.3, 134.2, 134.1, 133.2, 132.6, 130.2, 130.1, 130.0, 129.6, 129.5, 129.2, 128.8, 125.6, 122.7, 122.5, 120.8, 120.6 (arom), 33.2, 33.0, 32.1, 31.4, 31.2 (q, tBu), 29.2, 28.9, 28.4, 28.2, 28.1, 27.9 (tBu), 27.6, 27.3 (CH$_2$), 22.9, 14.2.

$^{31}$P NMR (121 MHz, C$_6$D$_6$) δ 17.90 (d, J=29.2 Hz), 16.13 (d, J=21.9 Hz), −0.59 (d, J=21.9 Hz), −0.73 (d, J=29.2 Hz).

Elemental analysis calculated for C$_{26}$H$_{32}$N$_2$P$_2$: C, 71.07; H, 7.63; N, 6.63; P, 14.66. Found: C, 71.15; H, 8.20; N, 6.63; P, 14.94.

Ligands

In the alkoxycarbonylation experiments which follow, the following ligands are used:

Ligand 1, Inventive Example

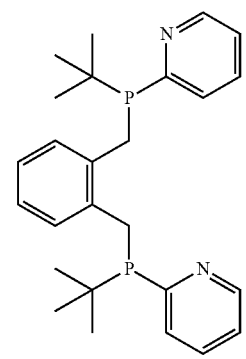

(1)

Ligand 18, Inventive Example

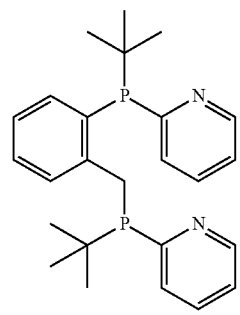

(18)

Ligand 3,
1,2-bis(di-tert-butylphosphinomethyl)benzene
(DTBPMB), comparative example

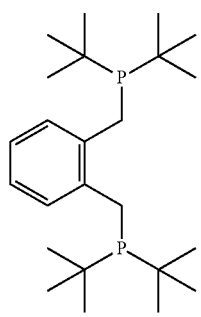

(3)

High-Pressure Experiments

Feedstocks:

Di-n-butene was also referred to as follows: dibutene, DNB or DnB.

Di-n-butene is an isomer mixture of C8 olefins which arises from the dimerization of mixtures of 1-butene, cis-2-butene and trans-2-butene. In industry, raffinate II or raffinate III streams are generally subjected to a catalytic oligomerization, wherein the butanes present (n/iso) emerge unchanged and the olefins present are converted fully or partly. As well as dimeric di-n-butene, higher oligomers (tributene C12, tetrabutene C16) generally also form, which have to be removed by distillation after the reaction.

Another process practised in industry for oligomerization of C4 olefins is called the "OCTOL process".

Within the patent literature, DE102008007081A1, for example, describes an oligomerization based on the OCTOL process. EP1029839A1 is concerned with the fractionation of the C8 olefins formed in the OCTOL process.

Technical di-n-butene consists generally to an extent of 5% to 30% of n-octenes, 45% to 75% of 3-methylheptenes, and to an extent of 10% to 35% of 3,4-dimethylhexenes. Preferred streams contain 10% to 20% n-octenes, 55% to 65% 3-methylheptenes, and 15% to 25% 3,4-dimethylhexenes.

para-Toluenesulphonic acid was abbreviated as follows: pTSA, PTSA or p-TSA. PTSA in this text always refers to para-toluenesulphonic acid monohydrate.

General Method for Performance of the High-Pressure Experiments

General Experiment Description for Reactions in Batchwise Mode:

The appropriate amounts of substrate, palladium salt, acid and alcohol are mixed under argon in a 50 ml Schlenk vessel while stirring with a magnetic stirrer.

A 100 ml steel autoclave from Parr provided with a gas inlet and a gas outlet valve, a digital pressure transducer, a temperature sensor and a ball valve, and an installed capillary for sampling, is freed of oxygen by means of vacuum and argon purging three times. Subsequently, the reaction solution from the Schlenk vessel is introduced by means of a capillary into the autoclave in an argon counterflow through the ball valve. Subsequently, either the appropriate amount of CO is injected at room temperature and then the autoclave is heated up to reaction temperature (reactions that are not run under constant pressure) or the autoclave is first heated up to reaction temperature and then the CO is injected by means of a burette connected to the autoclave by means of a pressure reducer. This burette is then filled with CO to about 100 bar and, during the reaction, supplies the CO required at a constant pressure. This burette has a dead volume of about 30 ml and is provided with a digital pressure transducer. Then the reaction is conducted at the required temperature for the required time while stirring. In the course of this, by means of software (Specview from SpecView Corporation) and a Parr 4870 process controller and a 4875 power controller, data for the pressure variation in the autoclave and in the gas burette are recorded. These data are used to generate Excel tables, which are used at a later stage to create diagrams which show gas consumptions and hence conversions over time. If required, via the capillary, the GC samples are collected and analysed. For this purpose, a suitable exact amount (2-10 ml) of isooctane as internal standard is also added to the Schlenk vessel before the reaction. These also give information about the course of the reaction. At the end of the reaction, the autoclave is cooled down to room temperature, the pressure is cautiously released, isooctane is added if necessary as internal standard, and a GC analysis or, in the case of new products, a GC-MS analysis is conducted.

General Experimental Method for Autoclave Experiments in Glass Vials:

A 300 ml Parr reactor is used. Matched to this is an aluminium block of corresponding dimensions which has been manufactured in-house and which is suitable for heating by means of a conventional magnetic stirrer, for example from Heidolph. For the inside of the autoclave, a round metal plate of thickness about 1.5 cm was manufactured, containing 6 holes corresponding to the external diameter of the glass vials. Matching these glass vials, they are equipped with small magnetic stirrers. These glass vials are provided with screw caps and suitable septa and charged, using a special apparatus manufactured by glass blowers, under argon with the appropriate reactants, solvents and catalysts and additives. For this purpose, 6 vessels are filled at the same time; this enables the performance of 6 reactions at the same temperature and the same pressure in one experiment. Then these glass vessels are closed with screw caps and septa, and a small syringe cannula of suitable size is used to puncture each of the septa. This enables gas exchange later in the reaction. These vials are then placed in the metal plate and these are transferred into the autoclave under argon. The autoclave is purged with CO and filled at room temperature with the CO pressure intended. Then, by means of the magnetic stirrer, under magnetic stirring, the autoclave is heated to reaction temperature and the reaction is conducted for the appropriate period. Subsequently, the autoclave is cooled down to room temperature and the pressure is slowly released. Subsequently, the autoclave is purged with nitrogen. The vials are taken from the autoclave, and a defined amount of a suitable standard is added. A GC analysis is effected, the results of which are used to determine yields and selectivities.

General Method for Experiments in the 12-Vial Autoclaves (600 ml Parr Autoclave):

Baked-out glass vials are each initially charged with di-n-butene (DnB) and methanol, and a solution of Pd(acac)$_2$ (0.5 mg, 0.0016 mmol) and ligand (0.0064 mmol) in 0.2 ml of methanol are added, as is H$_2$SO$_4$ (solution: 1 ml of H$_2$SO$_4$ in 50 ml MeOH). In the autoclave, the mixtures are purged twice with 10 bar of CO, CO is injected to the desired pressure, and the mixtures are stirred at the desired temperature for 20 h. After the reaction has ended, isooctane (internal standard) and 1 ml of EtOAc are added in each case. The organic phase is analysed by GC.

The yields of the reactions are determined by means of GC (isooctane as internal standard).

Analysis

GC analysis of the products from ethene: for the GC analysis, an Agilent 7890A gas chromatograph having a 30 m HP column is used. Temperature profile: 35° C., 10 min; 10° C./min to 200° C., 16.5 min; the injection volume is 1 µl with a split of 50:1. Retention time of methyl propionate: 6.158 min GC analysis of the products from tetramethylethene: for the GC analysis, an Agilent 7890A gas chromatograph having a 30 m HP column is used. Temperature profile: 35° C., 10 min; 10° C./min to 200° C., 16.5 min; the injection volume is 1 µl with a split of 50:1.

Retention time for tetramethylethylene and products: 7.436 min

Retention time for the ether: 11.391 min

Retention time for methyl 3,4-dimethylpentanoate: 17.269 min

GC analysis of di-n-butene: for the GC analysis, an Agilent 7890A gas chromatograph having a 30 m HP5 column is used. Temperature profile: 35° C., 10 min; 10° C./min to 200° C.; the injection volume is 1 µl with a split of 50:1.

Retention times for di-n-butene and products: 10.784-13.502 min

The esters formed from di-n-butene are referred to hereinafter as MINO (methyl isononanoate).

Retention time for ether products of unknown isomer distribution: 15.312, 17.042, 17.244, 17.417 min Retention time for iso-C9 esters 19.502-20.439 min (main peak: 19.990 min) Retention time for n-C9 esters: 20.669, 20.730, 20.884, 21.266 min.

Evaluation of the Experiments

For the evaluation of the catalytic experiments, particular indicators which permit comparison of the various catalyst systems are used hereinafter.

TON: turnover number, defined as moles of product per mole of catalyst metal, is a measure of the productivity of the catalytic complex.

TOE: turnover frequency, defined as TON per unit time for the attainment of a particular conversion, e.g. 50%. The TOE is a measure of the activity of the catalytic system.

The n selectivities reported hereinafter relate to the proportion of terminal methoxycarbonylation based on the overall yield of methoxycarbonylation products.

The n/iso ratio indicates the ratio of olefins converted terminally to esters to olefins converted internally to esters.

Methoxycarbonylation of Ethene

Scheme 4: Methoxycarbonylation of ethene.

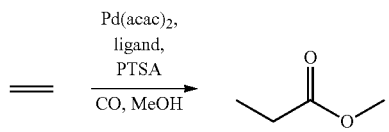

a) Ligand 1

A 25 ml steel autoclave was charged under argon with PdCl$_2$ (2.53 mg, 0.04 mol %), 1 (24.9 mg, 0.16 mol %) and MeOH (5 ml). Then ethene (1 g, 35.7 mmol) was introduced into the autoclave (monitoring the mass by means of a balance). The autoclave was heated up to 80° C. (pressure about 20 bar), then CO was injected to 30 bar. The reaction was conducted at 80° C. for 20 hours.

Subsequently, the autoclave was cooled down to room temperature and decompressed. The contents were transferred to a 50 ml Schlenk flask, and isooctane (5 ml) was added as internal GC standard. The yield was determined by means of GC analysis. (Yield: >99%).

b) Ligand 18

A 100 ml steel autoclave is charged with Pd(acac)$_2$ (6.52 mg, 0.04 mol %) and ligand 18 (36.1 mg, 0.16 mol %) and PTSA (61.1 mg, 0.6 mol %) and methanol (20 ml) under argon. Then 1.5 g (53.6 mmol) of ethylene (3.5 from Linde AG) are transferred into the autoclave. (Monitoring the mass of the autoclave). After the autoclave has been heated up to a reaction temperature of 80° C. (pressure about 10 bar), CO (30 bar) is injected at this temperature. At this temperature, the reaction is conducted for 20 hours. Then the autoclave is cooled down to room temperature and decompressed. The contents are transferred into a 50 ml Schlenk vessel, and isooctane (internal standard, 5.0 ml) is added. The yield and selectivity were determined by means of GC analysis. (Yield: 92%).

The inventive ligands 1 and 18 thus achieve a high yield in the methoxycarbonylation of ethene.

Methoxycarbonylation of Tetramethylethene in the Presence of PTSA

Scheme 5: Methoxycarbonylation of tetramethylethylene.

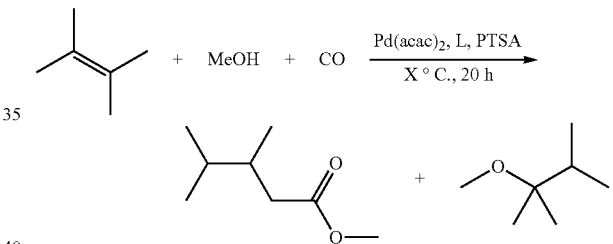

a) Reaction Temperature: 100° C.

(i) Ligand 3 (Comparative Example)

A 25 ml Schlenk vessel was charged with [Pd(acac)$_2$] (4.87 mg, 0.1 mol %), p-toluenesulphonic acid (PTSA) (24.32 mg, 0.8 mol %) and MeOH (8 ml). A 4 ml vial was charged with 3 (6.3 mg, 0.4 mol %), and a magnetic stirrer bar was added. Thereafter, 2 ml of the clear yellow solution and tetramethylethene (478 µl, 4 mmol) were added with a syringe. The vial was placed into a sample holder which was in turn inserted into a 300 ml Parr autoclave under an argon atmosphere. After the autoclave had been purged three times with nitrogen, the CO pressure was adjusted to 40 bar. The reaction proceeded at 100° C. for 20 hours. On conclusion of the reaction, the autoclave was cooled down to room temperature and cautiously decompressed. Isooctane (200 µl) was added as internal GC standard. Yield and regioselectivity were determined by means of GC. (Conversion: 40%, no ester product yield; ether product yield 38%).

(ii) Ligand 1

A 25 ml Schlenk vessel was charged with [Pd(acac)$_2$] (4.87 mg, 0.1 mol %), p-toluenesulphonic acid (PTSA) (24.32 mg, 0.8 mol %) and MeOH (8 ml). A 4 ml vial was charged with 1 (7.0 mg, 0.4 mol %), and a magnetic stirrer bar was added. Thereafter, 2 ml of the clear yellow solution and tetramethylethene (478 µl, 4 mmol) were added with a syringe.

The vial was placed into a sample holder which was in turn inserted into a 300 ml Parr autoclave under an argon atmosphere. After the autoclave had been purged three times with nitrogen, the CO pressure was adjusted to 40 bar. The reaction proceeded at 100° C. for 20 hours. On conclusion of the reaction, the autoclave was cooled down to room temperature and cautiously decompressed. Isooctane (200 µl) was added as internal GC standard. Yield and regioselectivity were determined by means of GC. (Conversion: 82%, ester product yield: 60%; ether product yield 20%).

b) Reaction Temperature: 120° C.

(i) Ligand 3 (Comparative Example)

A 25 ml Schlenk vessel was charged with [Pd(acac)$_2$] (4.87 mg, 0.1 mol %), p-toluenesulphonic acid (PTSA) (24.32 mg, 0.8 mol %) and MeOH (8 ml). A 4 ml vial was charged with 3 (6.3 mg, 0.4 mol %), and a magnetic stirrer bar was added. Thereafter, 2 ml of the clear yellow solution and tetramethylethene (478 µl, 4 mmol) were added with a syringe. The vial was placed into a sample holder which was in turn inserted into a 300 ml Parr autoclave under an argon atmosphere. After the autoclave had been purged three times with nitrogen, the CO pressure was adjusted to 40 bar. The reaction proceeded at 120° C. for 20 hours. On conclusion of the reaction, the autoclave was cooled down to room temperature and cautiously decompressed. Isooctane (200 µl) was added as internal GC standard. Yield and regioselectivity were determined by means of GC. (Conversion: 54%, no ester product yield; ether product yield 52%).

(ii) Ligand 1

A 25 ml Schlenk vessel was charged with [Pd(acac)$_2$] (4.87 mg, 0.1 mol %), p-toluenesulphonic acid (PTSA) (24.32 mg, 0.8 mol %) and MeOH (8 ml). A 4 ml vial was charged with 1 (7.0 mg, 0.4 mol %), and a magnetic stirrer bar was added. Thereafter, 2 ml of the clear yellow solution and tetramethylethene (478 µl, 4 mmol) were added with a syringe. The vial was placed into a sample holder which was in turn inserted into a 300 ml Parr autoclave under an argon atmosphere. After the autoclave had been purged three times with nitrogen, the CO pressure was adjusted to 40 bar. The reaction proceeded at 120° C. for 20 hours. On conclusion of the reaction, the autoclave was cooled down to room temperature and cautiously decompressed. Isooctane (200 µl) was added as internal GC standard. Yield and regioselectivity were determined by means of GC. (Conversion: >99%, ester product yield: 98%; no ether product yield).

As can be inferred from the results, ligand 1, even at 100° C. and CO pressure of 40 bar, leads to a higher ester product yield than comparative ligand 3. In addition, with ligand 1, a lower proportion of by-product (ether) is formed.

Methoxycarbonylation of Tetramethylene in the Presence of Trifluoromethanesulphonic Acid A 100 ml steel autoclave is charged with Pd(acac)$_2$ (4.87 mg, 0.04 mol %), ligand 1 (28.0 mg, 0.16 mol %) and CF$_3$SO$_2$OH (72.1 mg, 1.28 mol %) under argon. Then, under argon, MeOH (20 ml), isooctane (5 ml) and tetramethylethylene (4.8 ml, 40 mmol) are added. The autoclave is charged with 40 bar of CO at room temperature. The reaction is conducted at 120° C. for 20 hours. During this period, by means of an HPLC valve installed in the autoclave and an internal capillary in the autoclave, samples are taken at various times. These are analysed by means of GC analysis and the yields of the expected products are determined. After the sampling has ended, the autoclave is cooled down and decompressed, and a further final GC sample is taken and used to determine the yields. (98% yield of methyl 3,4-dimethylpentanoate).

Methoxycarbonylation of di-n-butene in the Presence of PTSA

Di-n-butene is a mixture of different olefin isomers having 8 carbon atoms. Its origin and general composition have already been elucidated above. The DnB used contained about 16% (w/w) n-octenes, 65% methylheptenes and 19% dimethylhexenes.

Di-n-butene is reacted with methanol to give methyl isononanoate (MINO).

The aim in the alkoxycarbonylation is to achieve very good yields at moderate to high selectivities for the linear product and ultimately to achieve good space-time yields for an industrial process with short reaction times up to the final yield.

Ligand 1:

A 100 ml steel autoclave is charged under argon with Pd(acac)$_2$ (5.85 mg, 0.04 mol %), 1 (33.5 mg, 0.16 mol %), MeOH (20 ml), 7.54 ml di-n-butene (48 mmol) and PTSA (para-toluenesulphonic acid monohydrate) (54.7 mg, 0.6 mol %). Then CO is injected into the autoclave to 40 bar at room temperature. The reaction is conducted at 120° C. for 20 hours. After the reaction, the autoclave is cooled down to room temperature and the pressure is released. 5 ml of isooctane are added to the solution as an internal standard. The yield and selectivity were determined by means of GC analysis. (Yield: 96%, n/iso: 73/27).

FIG. 1 shows the plot of yield against time for this reaction.

Ligand 3 (Comparative Example):

A 100 ml steel autoclave is charged under argon with [Pd(acac)$_2$] (5.85 mg, 0.04 mol %) and 3 (30.3 mg, 0.16 mol %). Subsequently, MeOH (30 ml) and di-n-butene (7.54 ml, 48 mmol) and PTSA (54.7 mg, 0.6 mol %) are added. The autoclave is charged at room temperature with CO of purity 4.7 to 40 bar and the reaction is conducted at 120° C. for 20 hours. Subsequently, the autoclave is cooled down and the pressure is slowly released. The contents of the autoclave are transferred to a Schlenk vessel. 5 ml of isooctane are added as internal standard and the yield and selectivity are determined by means of GC analysis (60% yield of MINO, n/iso: 93/7).

These experiments show that the inventive ligand 1 achieves a higher yield in the methoxycarbonylation of di-n-butene than the comparative ligand 3.

Methoxycarbonylation of di-n-butene in the Presence of Sulphuric Acid

Ligand 1:

A baked-out Schlenk flask is initially charged in each case with 0.04 mol % of Pd(acac)$_2$ (15 mg) and 0.16 mol % of 1 (105 mg). Then 12.4 ml (300 mmol) of methanol (technical grade), 18.8 ml (120 mmol) of di-n-butene and 32 µl (0.5 mol %) of H$_2$SO$_4$ (98%) are added and the mixture is transferred to a 100 ml autoclave. The autoclave is then purged twice with CO at 10 bar, charged with CO to 6 bar and heated to 100° C. Then the autoclave is charged with CO to 12 bar by means of a gas burette and stirred at 100° C. under constant CO pressure (12 bar) for 20 h. After the reaction has ended, isooctane (internal standard) and 10 ml of EtOAc are added. The organic phase is analysed by GC. The yield is 91%, the n selectivity 79%.

The gas consumption curve is shown in FIG. 2.

As can be inferred from the figure, the reaction is substantially complete after 20 hours. The gas absorption of about 20 bar corresponds to the yield of 91%.

Methoxycarbonylation of Ethylene and di-n-butene in the Presence of $H_2$

The experiments which follow show that, when the ligands according to the invention are used, the yield in the methoxycarbonylation of ethene or di-n-butene is not significantly impaired by contamination of the CO gas with $H_2$. The process according to the invention can accordingly also be conducted in the presence of small amounts of $H_2$.

a) Methoxycarbonylation of Ethene with Ligand 1

A 100 ml steel autoclave is charged with $Pd(acac)_2$ (6.5 mg, 0.04 mol %), 1 (37.7 mg, 0.16 mol %), PTSA (61.1 mg, 0.6 mol %) and MeOH (20 ml) under an argon atmosphere. Then ethene (3.5 Linde) (1.5 g, 53.6 mmol) is transferred into the autoclave (monitoring of mass by means of a balance). $H_2$ (3 bar) and CO (30 bar) are introduced into the autoclave at room temperature. Then the reaction is conducted at 80° C. for 20 hours. Subsequently, the autoclave is cooled down and decompressed. The contents are transferred to a 50 ml Schlenk vessel, and isooctane (internal standard, 3.0 ml) is added. The yield was determined by means of GC analysis. (Yield of methyl propionate: 99%).

b) Methoxycarbonylation of di-n-butene with Ligand 1

A 100 ml steel autoclave is charged under argon with $Pd(acac)_2$ (5.8 mg, 0.04 mol %), ligand 1 (33.5 mg, 0.16 mol %) and PTSA (54.7 mg, 0.6 mol %). Then MeOH (30 ml) and di-n-butene (7.54 ml, 48 mmol) are added under argon. The autoclave is charged with $H_2$ (3 bar) and CO (40 bar) at room temperature. After the reaction at 120° C. for 20 hours, the autoclave is cooled down and decompressed. The contents are transferred to a 50 ml Schlenk vessel, and isooctane (internal standard, 8 ml) is added. The yield and regioselectivity were determined by means of GC analysis (yield: 94%, n/iso: 74/26).

Methoxycarbonylation of Various Olefins with Ligands 3 and 1

Reaction conditions for ligand 3 (comparative example): a 25 ml Schlenk vessel is charged with a stock solution composed of $[Pd(acac)_2]$ (12.2 mg, 0.04 mol), 3 (63.1 mg, 0.16 mmol), PTSA (114 mg, 0.6 mmol) and MeOH (25 ml) under argon. A 4 ml glass vial provided with a magnetic stirrer is charged with 2 mmol of olefin. To this are added 1.25 ml of the previously prepared stock solution by means of a syringe. This vial is placed on a metal plate in a 300 ml Parr autoclave under argon. The autoclave is purged three times with CO and then CO is injected to 40 bar. Then, under magnetic stirring, the reaction is conducted at 120° C. for 20 h. This is followed by cooling and gradual release of the pressure. 0.2 ml of isooctane is added as an internal standard. Conversion and yield are determined by means of GC and GC-MS analysis.

Reaction conditions for ligand 1: a 25 ml Schlenk vessel is charged with a stock solution composed of $[Pd(acac)_2]$ (12.2 mg, 0.04 mol), 1 (69.8 mg, 0.16 mmol), PTSA (114 mg, 0.6 mmol) and MeOH (25 ml) under argon. A 4 ml glass vial provided with a magnetic stirrer is charged with 2 mmol of olefin. To this are added 1.25 ml of the previously prepared stock solution by means of a syringe. This vial is placed on a metal plate in a 300 ml Parr autoclave under argon. The autoclave is purged three times with CO and then CO is injected to 40 bar. Then, under magnetic stirring, the reaction is conducted at 120° C. for 20 h. This is followed by cooling and gradual release of the pressure. 0.2 ml of isooctane is added as an internal standard. Conversion and yield are determined by means of GC and GC-MS analysis.

For the GC analysis, in both cases, an Agilent 7890A gas chromatograph having a 30 m HP column is used. Temperature profile: 35° C., 10 min; 10° C./min to 285° C., 285° C. 5 min; the injection volume is 1 μl with a split of 50:1.

The results are shown in the two tables which follow.

TABLE 3

Substrate screening with ligands 3 (comparative example) and 1 (inventive ligand)

| Substrate | Ligand | Ester yield [%] (n/iso) |
|---|---|---|
| Rt: 24.232-25.903 | 3<br>1* | 10<br>94 (n,n/n, iso/iso,iso = 47/35/18) |
| Rt: 22.285 | 3<br>1* | 19<br>89 |
| Rt: 26.7-27.838 | 3<br>1* | 30 (92/8)<br>96 (72/28) |
| Rt: 19.252-20.245 | 3<br>1* | 0<br>95$^a$ (19/81) |
| Rt: iso: 21.483, n: 22.327 | 3<br>1* | 0<br>65 (84/16) |
| Rt: iso: 21.22, n: 222.062 | 3<br>1* | 8<br>91 (70/30) |
| Rt: 22.212 | 3<br>1* | 34 (100/0)<br>88 (100/0) |
| Rt: 26.113 | 3<br>1* | 25 (100/0)<br>97 (100/0) |
| Rt: 22.279 | 3<br>1* | 60 (100/0)<br>95 (100/0) |

TABLE 3-continued

Substrate screening with ligands 3 (comparative example) and 1 (inventive ligand)

| Substrate | Ligand | Ester yield [%] (n/iso) |
|---|---|---|
| 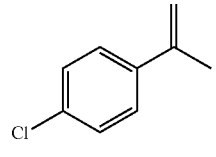<br>Rt: 24.477 | 3<br>1* | 28 (100/0)<br>97 (100/0) |
| 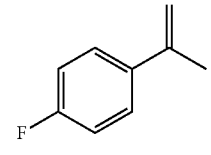<br>Rt: 22.334 | 3<br>1* | 23 (100/0)<br>96 (100/0) |
| 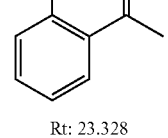<br>Rt: 23.328 | 3<br>1* | 35 (100/0)<br>96 (100/0) |
| 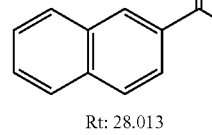<br>Rt: 28.013 | 3<br>1* | 30 (100/0)<br>97 (100/0) |
| 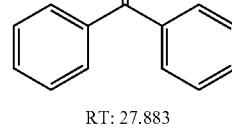<br>RT: 27.883 | 3<br>1* | 5 (100/0)<br>99 (100/0) |
| 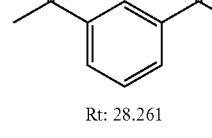<br>Rt: 28.261 | 3<br>1* | 10 (100/0)<br>99 (100/0) |
| 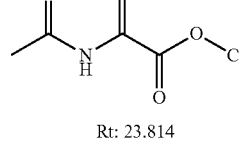<br>Rt: 23.814 | 3<br>1* | 0<br>100 (100/0) |
| 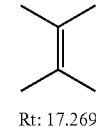<br>Rt: 17.269 | 3<br>1* | 0<br>98 |

<sup>a</sup>GC yield.
Rt: retention time in minutes;
*inventive ligand

TABLE 4

Further substrates in screening with the ligands 3 (comparative example) and 1 (inventive ligand) in direct comparison

| Substrate | Ligand | Ester yield (n/iso) [%] |
|---|---|---|
| 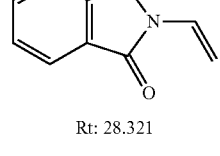<br>Rt: 28.321 | 3<br>1* | 90<br>100 |
| 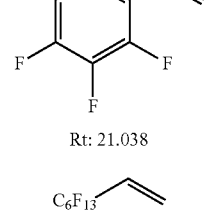<br>Rt: 21.038 | 3<br>1* | 100<br>100 |
| C$_6$F$_{13}$ <br>Rt: 17.822 | 3<br>1* | 100<br>100 |
| 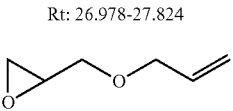<br>Rt: 26.978-27.824 | 3<br>1* | 0<br>40 |
| 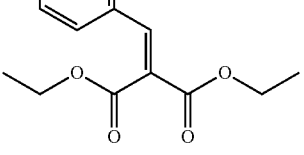<br>Rt: 18.514 | 3<br>1* | 100<br>100 |
| <br>Rt: 27.32 | 3<br>1* | 100<br>100 |

TABLE 4-continued

Further substrates in screening with the ligands 3 (comparative example) and 1 (inventive ligand) in direct comparison

| Substrate | Ligand | Ester yield (n/iso) [%] |
|---|---|---|
| 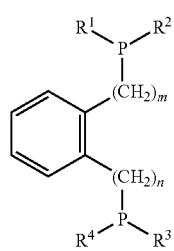 | 3<br>1* | 100<br>100 |

Rt: retention time in minutes
*inventive ligand

As the results show, it is possible by the process according to the invention to convert a multitude of different ethylenically unsaturated compounds. In most cases, the inventive ligand 1 shows a better yield of ester, a lower isomerization level, lower by product formation and better n/iso selectivity than the comparative ligand 3.

The invention claimed is:

1. Compound of formula (I)

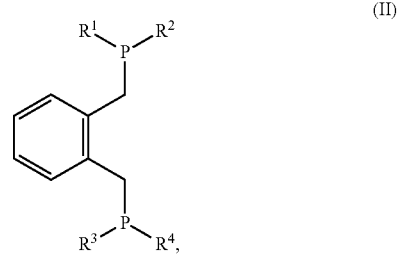

where m and n are each independently 0 or 1;

$R^1$ and $R^3$ are each a —$(C_3$-$C_{20})$-heteroaryl radical;

$R^2$ and $R^4$ are each independently selected from —$(C_1$-$C_{12})$-alkyl, —$(C_3$-$C_{12})$-cycloalkyl, —$(C_3$-$C_{12})$-heterocycloalkyl, —$(C_6$-$C_{20})$-aryl, —$(C_3$-$C_{20})$-heteroaryl; and $R^1$, $R^2$, $R^3$, $R^4$, if they are —$(C_1$-$C_{12})$-alkyl, —$(C_3$-$C_{12})$-cycloalkyl, —$(C_3$-$C_{12})$-heterocycloalkyl, —$(C_6$-$C_{20})$-aryl or —$(C_3$-$C_{20})$-heteroaryl, may each independently be substituted by one or more substituents selected from —$(C_1$-$C_{12})$-alkyl, —$(C_3$-$C_{12})$-cycloalkyl, —$(C_3$-$C_{12})$-heterocycloalkyl, —O—$(C_1$-$C_{12})$-alkyl, —O—$(C_1$-$C_{12})$-alkyl-$(C_6$-$C_{20})$-aryl, —O—$(C_3$-$C_{12})$-cycloalkyl, —S—$(C_1$-$C_{12})$-alkyl, —S—$(C_3$-$C_{12})$-cycloalkyl, —COO—$(C_1$-$C_{12})$-alkyl, —COO—$(C_3$-$C_{12})$-cycloalkyl, —CONH—$(C_1$-$C_{12})$-alkyl, —CONH—$(C_3$-$C_{12})$-cycloalkyl, —CO—$(C_1$-$C_{12})$-alkyl, —CO—$(C_3$-$C_{12})$-cycloalkyl, —N—[$(C_1$-$C_{12})$-alkyl]$_2$, —$(C_6$-$C_{20})$-aryl, —$(C_6$-$C_{20})$-aryl-$(C_1$-$C_{12})$-alkyl, —$(C_6$-$C_{20})$-aryl-O—$(C_1$-$C_{12})$-alkyl, —$(C_3$-$C_{20})$-heteroaryl, —$(C_3$-$C_{20})$-heteroaryl-$(C_1$-$C_{12})$-alkyl, —$(C_3$-$C_{20})$-heteroaryl-O—$(C_1$-$C_{12})$-alkyl, —COOH, —OH, —SO$_3$H, —NH$_2$, halogen.

2. Compound according to claim 1,
of one of the formulae (II) and (III)

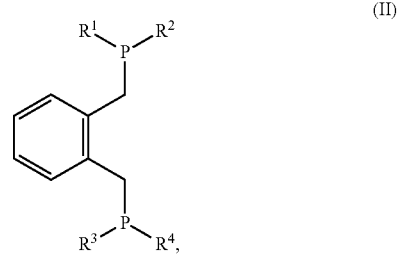

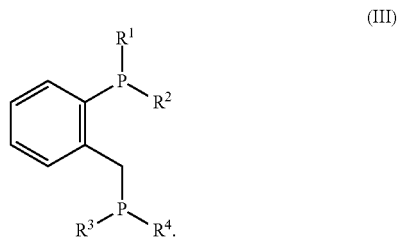

3. Compound according to claim 1,
where the $R^2$, $R^4$, or both the $R^2$ and $R^4$ radicals are a —$(C_3$-$C_{20})$-heteroaryl radical.

4. Compound according to claim 1,
where
$R^2$ and $R^4$ are each independently selected from —$(C_1$-$C_{12})$-alkyl, —$(C_3$-$C_{12})$-cycloalkyl, —$(C_3$-$C_{12})$-heterocycloalkyl, —$(C_6$-$C_{20})$-aryl.

5. Compound according to claim 1,
where
$R^2$ and $R^4$ are each independently selected from —$(C_1$-$C_{12})$-alkyl.

6. Compound according to claim 1,
where $R^1$, $R^2$, $R^3$, $R^4$, if they are a heteroaryl radical, are each independently selected from furyl, thienyl, pyrrolyl, oxazolyl, isoxazolyl, thiazolyl, isothiazolyl, imidazolyl, pyrazolyl, furazanyl, tetrazolyl, pyridyl, pyridazinyl, pyrimidyl, pyrazinyl, benzofuranyl, indolyl, isoindolyl, benzimidazolyl, quinolyl, isoquinolyl.

7. Compound according to claim 1,
of one of the formulae (1) and (18)

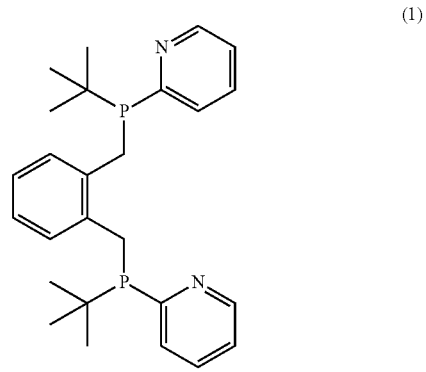 [SMILES: CC(C)(C)P(Cc1ccccc1CP(c1ccccn1)C(C)(C)C)c1ccccn1]

-continued

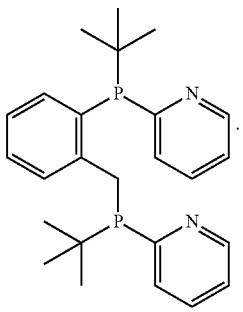
(18)

8. Complex comprising Pd and a compound according to claim 1.

9. Process comprising the following process steps:
a) initially charging an ethylenically unsaturated compound;
b) adding a compound of formula (I)

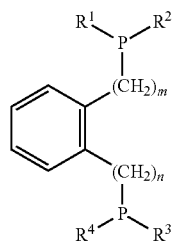
(I)

where
m and n are each independently 0 or 1;
$R^1$ and $R^3$ are each a —$(C_3$-$C_{20})$-heteroaryl radical;
$R^2$ and $R^4$ are each independently selected from —$(C_1$-$C_{12})$-alkyl, —$(C_3$-$C_{12})$-cycloalkyl, —$(C_3$-$C_{12})$-heterocycloalkyl, —$(C_6$-$C_{20})$-aryl, —$(C_3$-$C_{20})$-heteroaryl; and
$R^1$, $R^2$, $R^3$, $R^4$, if they are —$(C_1$-$C_{12})$-alkyl, —$(C_3$-$C_{12})$-cycloalkyl, —$(C_3$-$C_{12})$-heterocycloalkyl, —$(C_6$-$C_{20})$-aryl or —$(C_3$-$C_{20})$-heteroaryl,
may each independently be substituted by one or more substituents selected from —$(C_1$-$C_{12})$-alkyl, —$(C_3$-$C_{12})$-cycloalkyl, —$(C_3$-$C_{12})$-heterocycloalkyl, —O—$(C_1$-$C_{12})$-alkyl, —O—$(C_1$-$C_{12})$-alkyl-$(C_6$-$C_{20})$-aryl, —O—$(C_3$-$C_{12})$-cycloalkyl, —S—$(C_1$-$C_{12})$-alkyl, —S—$(C_3$-$C_{12})$-cycloalkyl, —COO—$(C_1$-$C_{12})$-alkyl, —COO—$(C_3$-$C_{12})$-cycloalkyl, —CONH—$(C_1$-$C_{12})$-alkyl, —CONH—$(C_3$-$C_{12})$-cycloalkyl, —CO—$(C_1$-$C_{12})$-alkyl, —CO—$(C_3$-$C_{12})$-cycloalkyl, —N—[$(C_1$-$C_{12})$-alkyl]$_2$, —$(C_6$-$C_{20})$-aryl, —$(C_6$-$C_{20})$-aryl-$(C_1$-$C_{12})$-alkyl, —$(C_6$-$C_{20})$-aryl-O—$(C_1$-$C_{12})$-alkyl, —$(C_3$-$C_{20})$-heteroaryl, —$(C_3$-$C_{20})$-heteroaryl-$(C_1$-$C_{12})$-alkyl, —$(C_3$-$C_{20})$-heteroaryl-O—$(C_1$-$C_{12})$-alkyl, —COOH, —OH, —$SO_3H$, —$NH_2$, or halogen, and a compound comprising Pd,
or adding a complex according to claim 8;
c) adding an alcohol;
d) feeding in CO;
e) heating the reaction mixture, with conversion of the ethylenically unsaturated compound to an ester.

10. Process according to claim 9,
wherein the ethylenically unsaturated compound comprises 2 to 30 carbon atoms and optionally one or more functional groups selected from carboxyl, thiocarboxyl, sulpho, sulphinyl, carboxylic anhydride, imide, carboxylic ester, sulphonic ester, carbamoyl, sulphamoyl, cyano, carbonyl, carbonothioyl, hydroxyl, sulphhydryl, amino, ether, thioether, aryl, heteroaryl or silyl groups and/or halogen substituents.

11. Process according to claim 9,
wherein the ethylenically unsaturated compound is selected from ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, 1-octene, 2-octene, di-n-butene, and mixtures thereof.

12. Process according to claim 9,
wherein the compound comprising Pd in process step b) is selected from palladium dichloride, palladium(II) acetylacetonate, palladium(II) acetate, dichloro(1,5-cyclooctadiene)palladium(II), bis(dibenzylideneacetone)palladium, bis(acetonitrile)dichloropalladium(II), palladium(cinnamyl) dichloride.

13. Process according to claim 9,
wherein the alcohol in process step c) is selected from methanol, ethanol, 1-propanol, 1-butanol, 1-pentanol, 1-hexanol, 2-propanol, tert-butanol, 3-pentanol, cyclohexanol, phenol, and mixtures thereof.

14. A process for catalysis of an alkoxycarbonylation reaction, comprising: introducing a compound of formula (I)

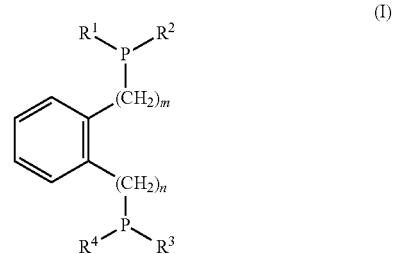
(I)

where
m and n are each independently 0 or 1;
$R^1$ and $R^3$ are each a —$(C_3$-$C_{20})$-heteroaryl radical;
$R^2$ and $R^4$ are each independently selected from —$(C_1$-$C_{12})$-alkyl, —$(C_3$-$C_{12})$-cycloalkyl, —$(C_3$-$C_{12})$-heterocycloalkyl, —$(C_6$-$C_{20})$-aryl, —$(C_3$-$C_{20})$-heteroaryl; and
$R^1$, $R^2$, $R^3$, $R^4$, if they are —$(C_1$-$C_{12})$-alkyl, —$(C_3$-$C_{12})$-cycloalkyl, —$(C_3$-$C_{12})$-heterocycloalkyl, —$(C_6$-$C_{20})$-aryl or —$(C_3$-$C_{20})$-heteroaryl,
may each independently be substituted by one or more substituents selected from —$(C_1$-$C_{12})$-alkyl, —$(C_3$-$C_{12})$-cycloalkyl, —$(C_3$-$C_{12})$-heterocycloalkyl, —O—$(C_1$-$C_{12})$-alkyl, —O—$(C_1$-$C_{12})$-alkyl-$(C_6$-$C_{20})$-aryl, —O—$(C_3$-$C_{12})$-cycloalkyl, —S—$(C_1$-$C_{12})$-alkyl, —S—$(C_3$-$C_{12})$-cycloalkyl, —COO—$(C_1$-$C_{12})$-alkyl, —COO—$(C_3$-$C_{12})$-cycloalkyl, —CONH—$(C_1$-$C_{12})$-alkyl, —CONH—$(C_3$-$C_{12})$-cycloalkyl, —CO—$(C_1$-$C_{12})$-alkyl, —CO—$(C_3$-$C_{12})$-cycloalkyl, —N—[$(C_1$-$C_{12})$-alkyl]$_2$, —$(C_6$-$C_{20})$-aryl, —$(C_6$-$C_{20})$-aryl-$(C_1$-$C_{12})$-alkyl, —$(C_6$-$C_{20})$-aryl-O—$(C_1$-$C_{12})$-alkyl, —$(C_3$-$C_{20})$-heteroaryl, —$(C_3$-$C_{20})$-heteroaryl-$(C_1$-$C_{12})$-alkyl, —$(C_3$-$C_{20})$-heteroaryl-O—$(C_1$-$C_{12})$-alkyl, —COOH, —OH, —$SO_3H$, —$NH_2$, or halogen, or a complex according to claim 8.

* * * * *